US012642601B2

(12) United States Patent
Haubert

(10) Patent No.: US 12,642,601 B2
(45) Date of Patent: Jun. 2, 2026

(54) POSITION SENSING AND BREAKAWAY MECHANISM

(71) Applicant: CANON U.S.A., INC., Melville, NY (US)

(72) Inventor: Zachary Hamilton Haubert, Somerville, MA (US)

(73) Assignee: Canon U.S.A., Inc., Melville, NY (US)

( * ) Notice: Subject to any disclaimer, the term of this patent is extended or adjusted under 35 U.S.C. 154(b) by 42 days.

(21) Appl. No.: 18/648,194

(22) Filed: Apr. 26, 2024

(65) Prior Publication Data

US 2025/0169888 A1 May 29, 2025

Related U.S. Application Data

(60) Provisional application No. 63/603,489, filed on Nov. 28, 2023.

(51) Int. Cl.
*A61B 34/20* (2016.01)
*A61B 34/00* (2016.01)
(Continued)

(52) U.S. Cl.
CPC ............ *A61B 34/20* (2016.02); *G01B 11/002* (2013.01); *A61B 2034/2055* (2016.02);
(Continued)

(58) Field of Classification Search
CPC .................... A61B 34/20; A61B 34/30; A61B 2017/00469; A61B 2034/2055; A61B 2034/301; A61B 2034/715; A61B 2090/064; A61B 2034/2051; A61B 2034/303; A61B 34/71; A61B 2090/066;
(Continued)

(56) References Cited

U.S. PATENT DOCUMENTS 5,195,978 A 3/1993 Schiffer
5,604,826 A 2/1997 Kajita
(Continued)

FOREIGN PATENT DOCUMENTS

JP 200339630 A 12/2003
JP 2022019740 A 1/2022
(Continued)

*Primary Examiner* — Wade Miles
*Assistant Examiner* — Jaewook Jung
(74) *Attorney, Agent, or Firm* — Canon U.S.A., Inc. I.P. Division

(57) ABSTRACT

An apparatus can include an actuator configured to move a wire along a longitudinal direction, a tractor that is connected to the wire and is configured to move the wire along the longitudinal direction, a driving unit, a first arm connected to the driving unit that drives the first arm to the longitudinal direction, a board connected to the first arm, a second arm connected to the wire, a plurality of sensors that can include at least a first sensor and a second sensor arranged at a different position from each other along a direction perpendicular to the longitudinal direction, at least one positional sensor configured to detect light from the board, a support member configured to support at least one positional sensor, and a breakaway mechanism that can include a breakaway connector configured to connect and disconnect the first arm and the second arm.

27 Claims, 28 Drawing Sheets

1006

Breakaway
mechanism 1206

(51) Int. Cl.

| | |
|---|---|
| *A61B 34/30* | (2016.01) |
| *A61B 90/00* | (2016.01) |
| *A61M 25/01* | (2006.01) |
| *G01B 11/00* | (2006.01) |

(52) U.S. Cl.
CPC ... *A61B 2034/301* (2016.02); *A61B 2034/715* (2016.02); *A61B 2090/064* (2016.02); *A61M 2025/0166* (2013.01)

(58) Field of Classification Search
CPC ................ A61F 2/9517; G01B 11/002; A61M 2025/0166
See application file for complete search history.

(56) References Cited

U.S. PATENT DOCUMENTS

| | | | |
|---|---|---|---|
| 9,839,481 | B2 | 12/2017 | Blumenkranz |
| 9,918,659 | B2 | 3/2018 | Chopra |
| 10,791,908 | B2 | 10/2020 | Au |
| 10,806,434 | B2 | 10/2020 | Vetter |
| 11,007,641 | B2 | 5/2021 | Takagi |
| 11,109,833 | B2 | 9/2021 | Nystrom |
| 11,266,466 | B2 | 3/2022 | Larkin |
| 11,278,357 | B2 | 3/2022 | Ummalaneni |
| 11,510,736 | B2 | 11/2022 | Rafii-Tari |
| 11,622,828 | B2 | 4/2023 | Kincaid |
| 11,690,683 | B2 | 7/2023 | Bell |
| 11,723,606 | B2 | 8/2023 | Chopra |
| 11,723,729 | B2 | 8/2023 | Shelton, IV |
| 2001/0019487 | A1 | 9/2001 | Honguh |
| 2012/0179032 | A1 | 7/2012 | Bromander |
| 2013/0123802 | A1 | 5/2013 | Comber |
| 2014/0028863 | A1 | 1/2014 | Takei |
| 2014/0039305 | A1 | 2/2014 | Tal |
| 2015/0133959 | A1 | 5/2015 | Kato |
| 2016/0174816 | A1 | 6/2016 | Choset |
| 2017/0332999 | A1 | 11/2017 | Coolidge |
| 2018/0055589 | A1 | 3/2018 | Joseph |
| 2019/0015978 | A1 | 1/2019 | Takagi |
| 2021/0228289 | A1 | 7/2021 | Rohr Daniel |
| 2021/0259521 | A1 | 8/2021 | Hwang |
| 2021/0259794 | A1 | 8/2021 | Kato |
| 2021/0369366 | A1 | 12/2021 | Hwang |
| 2022/0032456 | A1 | 2/2022 | Kose |
| 2022/0040450 | A1* | 2/2022 | Haubert ................ A61B 34/71 |
| 2022/0142725 | A1 | 5/2022 | Pocrnich |
| 2022/0202273 | A1 | 6/2022 | Ninni |
| 2022/0203075 | A1 | 6/2022 | Murphy |
| 2022/0313962 | A1 | 10/2022 | Kim |
| 2023/0099522 | A1 | 3/2023 | Moller |
| 2023/0137954 | A1 | 5/2023 | George |
| 2023/0201522 | A1 | 6/2023 | Hwang |

FOREIGN PATENT DOCUMENTS

| | | |
|---|---|---|
| JP | 2022033697 A | 3/2022 |
| WO | 2015092870 A1 | 6/2015 |

* cited by examiner

FIG.2
Homing Channel
State A: High signal tells tractor to move positive direction to find zero
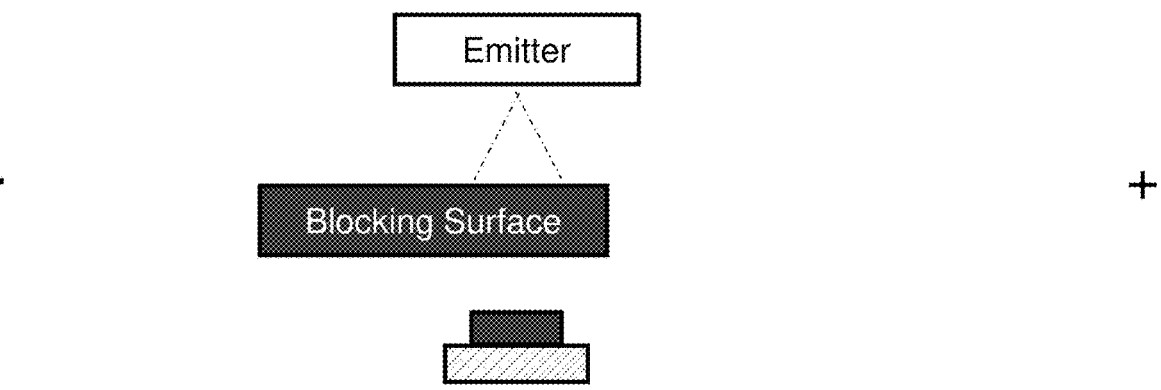
State B: Low signal tells tractor to move negative direction to find zero
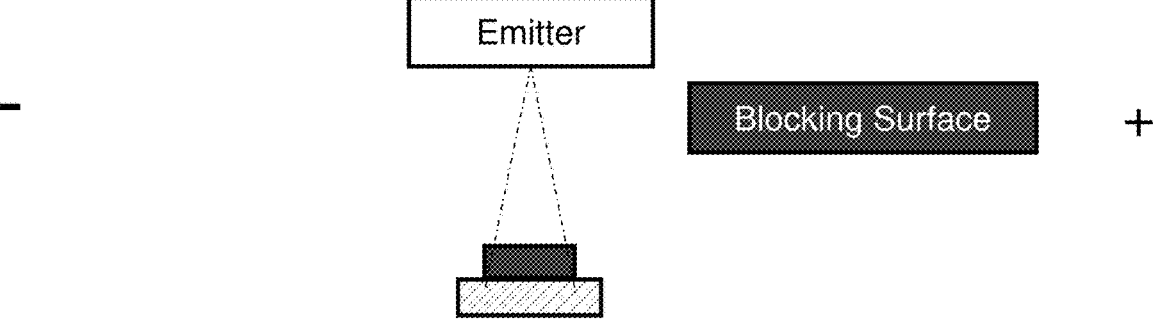

Limit Channel

State A: High signal tells tractor to move positive direction to find zero

FIG.6
Homing Channel
State A: High signal tells tractor to move positive direction to find zero
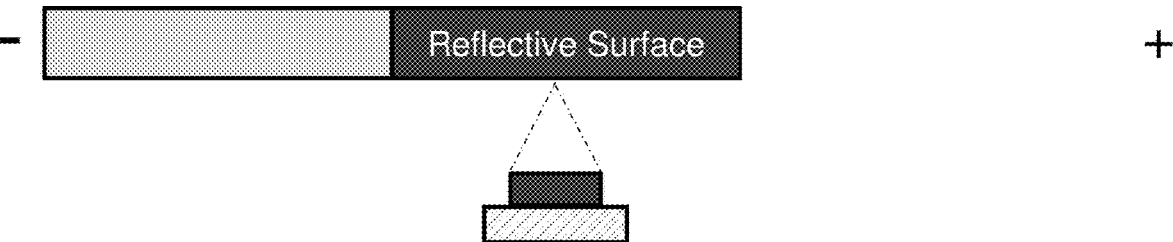
State B: Low signal tells tractor to move negative direction to find zero
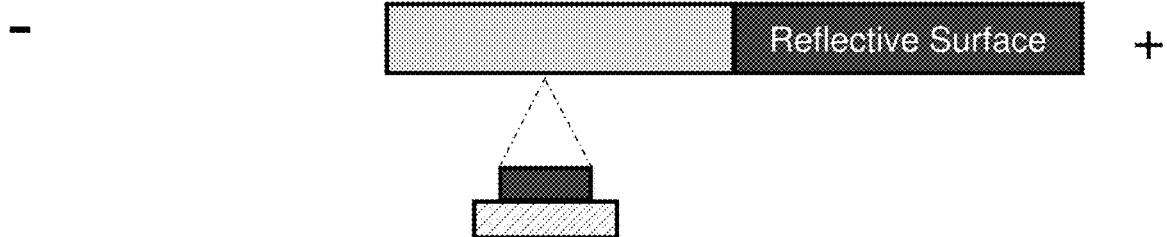

Limit Channel

FIG.8
Center of Travel/Home Position
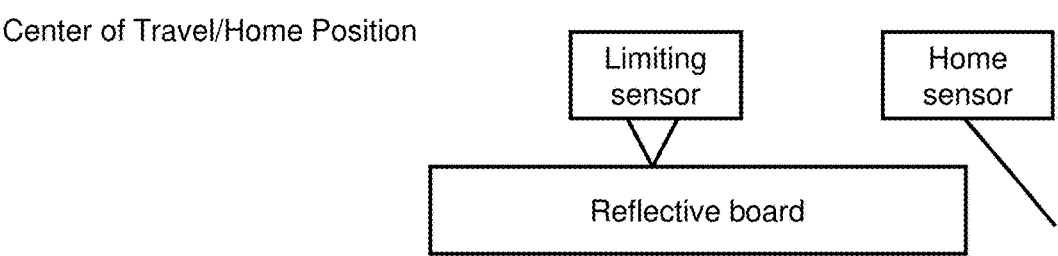
Positive Travel Limit
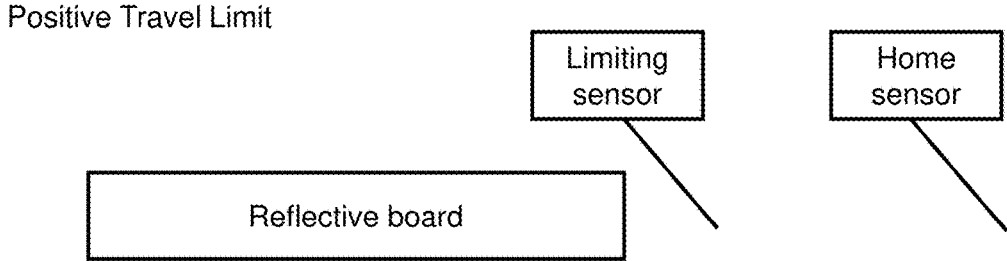
Negative Travel Limit
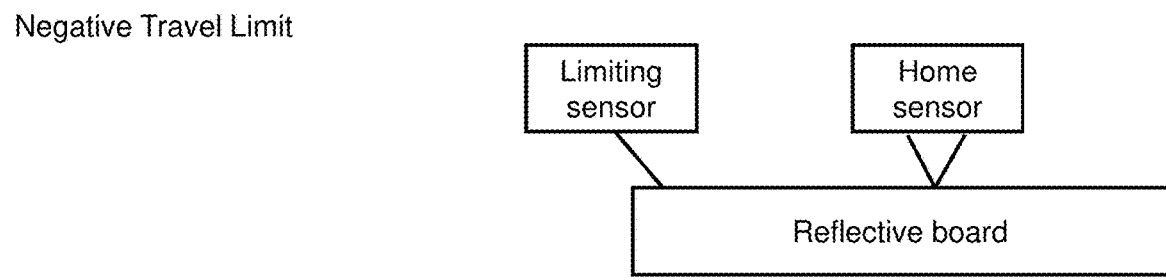

Blocking opto-sensor

Reflective opto-sensor

FIG.13
1022
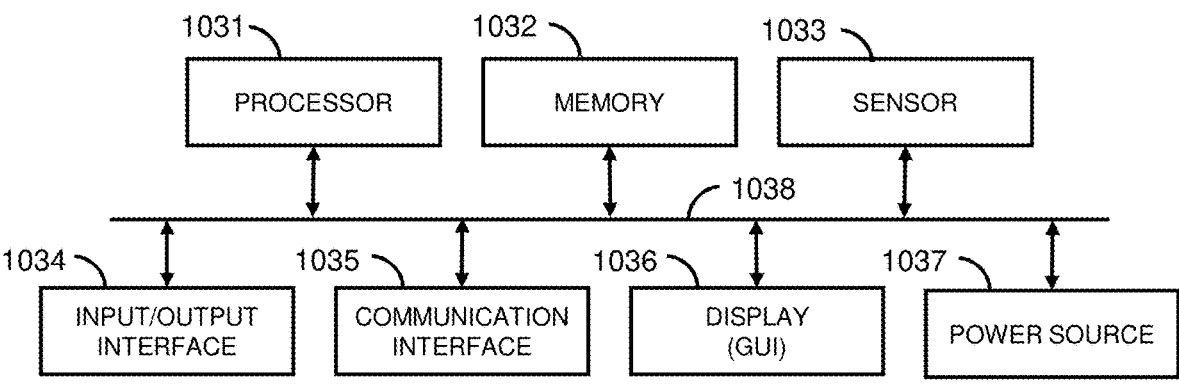

1002

A

1005

1004

1002B

1002A

1040

1042

1044

1046

1002C

Breakaway
mechanism 1206

Limit Sensing
Edges

Homing Sensing Edge

Homing Sensing Edge

Limit Sensing Edges

Homing Sensing Edge

Photo Sensor

First Arm

Reflective Board

FIG.26

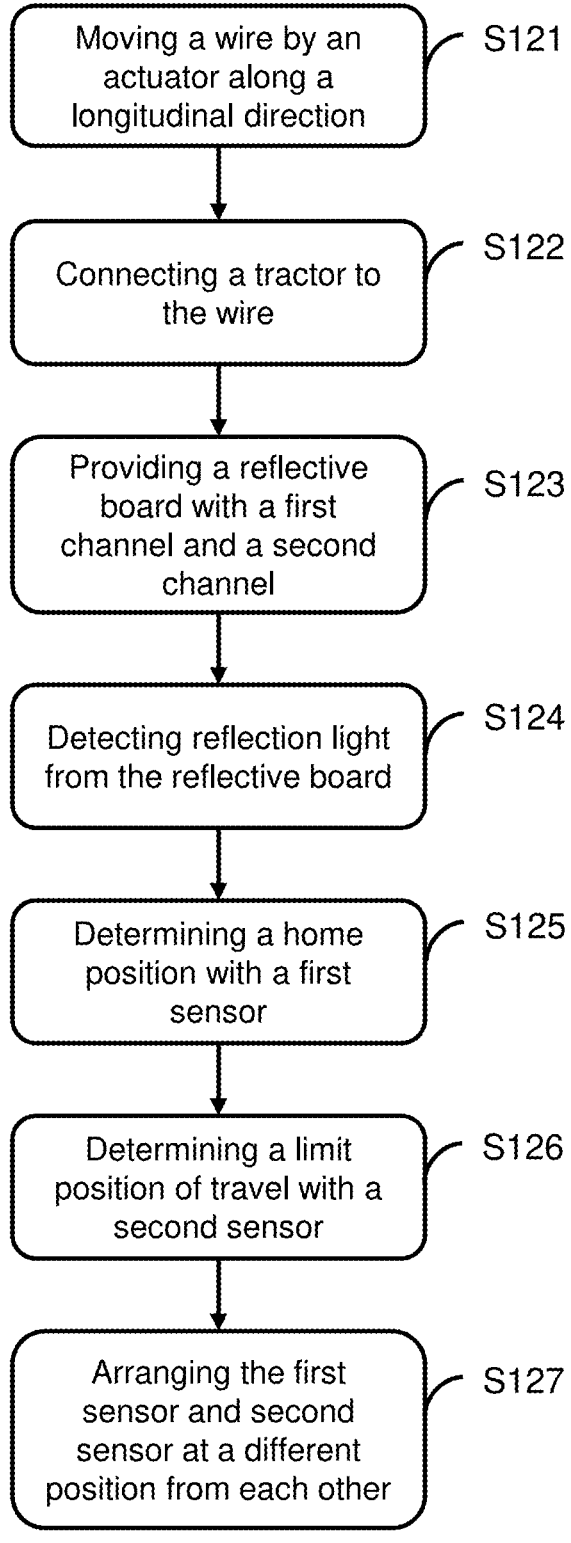

Moving a wire by an actuator along a longitudinal direction — S121

Connecting a tractor to the wire — S122

Providing a reflective board with a first channel and a second channel — S123

Detecting reflection light from the reflective board — S124

Determining a home position with a first sensor — S125

Determining a limit position of travel with a second sensor — S126

Arranging the first sensor and second sensor at a different position from each other — S127

Moving a wire by an actuator along a longitudinal direction — S131

Connecting a tractor to the wire — S132

Connecting a first arm to a driving unit — S133

Connecting a second arm to the wire — S134

Providing a breakaway mechanism — S135

Supporting one or more positional sensors — S136

Reflecting light with a reflective board — S137

Moving a wire by an actuator along a longitudinal direction — S141

Connecting a tractor to the wire — S142

Connecting a first arm to a driving unit — S143

Connecting a second arm to the wire — S144

Providing a breakaway mechanism — S145

Supporting one or more positional sensors — S146

Blocking light with a blocking board — S147

POSITION SENSING AND BREAKAWAY MECHANISM

CROSS-REFERENCE TO RELATED APPLICATIONS

This application claims the benefit of priority from U.S. Provisional Patent Application No. 63/603,489, filed Nov. 28, 2023, which is hereby incorporated by reference herein in its entirety.

BACKGROUND

Field of the Disclosure

The present disclosure generally relates to position sensing and breakaway mechanisms and, more particularly, to apparatuses, methods, and mediums for position sensing using various combinations of sensors, couplers, reflective boards, blocking boards, breakaway mechanisms, and other components.

Description of the Related Art

Position sensing is useful in various applications including medical, non-medical, industrial, automotive, logistics, agriculture, or other areas to increase accuracy of device or component positional detection, measurement, movement, or the like. Position sensors can be mechanical, acoustic, optical, electromagnetic, magnetic, or combinations thereof, and generally track the location or movement of a device through an object by various sensing techniques including reflective, retro reflective, Hall effect principles, resistive sensing, electrical circuitry, mechanical switches, or other sensing procedures. Reflective or retroreflective position sensors use a target to reflect light back to determine position, location, orientation, or other parameters.

Flexible or elongate tools, instruments, or other devices, e.g., catheters, endoscopes, colonoscopes, bronchoscopes, ablation devices, or other devices, can be used to look inside an object, where an instrument is passed through the tool to examine or treat an area in the object, such as a patient or the like.

A continuum robot, snake robot, robotic assembly, snake endoscopic assembly, snake catheter assembly, or other types of assemblies are exemplary arrangements or configurations that can implement a flexible device to carry out medical procedures including imaging, diagnostic, endoscopic, biopsy, therapeutic, surgical, image guided therapy, or other procedures. Endoscopic procedures include colonoscopy (bowel), gastroscopy (stomach), cystoscopy (bladder), bronchoscopy (airways of the lung), laparoscopy (abdomen), and other types of procedures.

These configurations may have bendable structures equipped with operation wires and a rotational drive assembly to impart translational, rotational, or other types of movement to the operation wires of a steerable catheter, endoscope, or other flexible device. The drive assembly can be releasably connected to the catheter and a breakaway mechanism can be used so the drive assembly disconnects from the catheter in response to a breakaway force.

A snake catheter assembly, for example, can include a steerable catheter actuated with push-pull wires, a motorized actuator for driving catheter tip motions through the push-pull wires, and a controller that translates user/software commands into actuator motion, and other elements.

By actuating wires with both push and pull directions, tensile and contraction forces on the wires can lead to failure including wire anchor fracturing (wire anchors being the bonding mechanism between the wire and the catheter tip), wire prolapse and protrusion, and excessive lateral bending force to internal tissues such as lung tissues or the like. The wires may be broken at unexpected positions while the wires are released.

Breakaway mechanisms can prevent transmission of excessive force from the actuator motor to the drive wire. However, when breakaway occurs, there is a need for the tractor to return to its home position.

Similarly, in a case where a configuration is powered on during a breakaway state, there is no mechanism for ensuring the breakaway is recoupled.

There is a need to ensure breakaway is re-engaged and to integrate home and travel limit sensors together to prevent the chance of a tractor experience of a crash situation where the tractor gets jammed requiring maintenance.

SUMMARY

The present disclosure advantageously provides solutions to ensure breakaway is re-engaged and to integrate home and travel limit sensors together to prevent the chance of a tractor experience in a crash situation where the tractor gets jammed.

According to some embodiments, an apparatus can include an actuator configured to move a wire along a longitudinal direction, a tractor that is connected to the wire and is configured to move the wire along the longitudinal direction, a driving unit, a first arm connected to the driving unit that drives the first arm to the longitudinal direction, a board connected to the first arm, a second arm connected to the wire, a plurality of sensors that can include at least a first sensor and a second sensor arranged at a different position from each other along a direction perpendicular to the longitudinal direction, at least one positional sensor configured to detect light from the board, a support member configured to support at least one positional sensor, and a breakaway mechanism that can include a breakaway connector configured to connect and disconnect the first arm and the second arm.

The breakaway mechanism can be configured to disconnect the actuator and the tractor in a case where an applied force is greater than a predetermined value. The breakaway mechanism can include a breakaway sensor configured to detect when breakaway occurs. In a case where breakaway detected by the breakaway sensor, a recovery and homing routine can be initiated, and/or an error state can be initiated that can prompt a service technician or other to diagnose the apparatus. The breakaway mechanism can be configured to return the tractor to home position in a case where breakaway occurs. The second arm can be moved to the longitudinal direction while the first arm and the second arm is connected by the breakaway connector and the first arm is driven by the driving unit.

The board can include a first channel and a second channel. The first channel and the second channel of the board can each have a length, wherein the length of the first channel is shorter than the length of the second channel. The first channel and the second channel of the board can be configured to move along with movement of the tractor.

The at least one positioning sensor can include at least a first sensor and a second sensor that are arranged at a different position from each other along a direction perpendicular to the longitudinal direction. The wire can include a plurality of wires. The apparatus can include one or more force sensors configured to measure push and pull forces on the wire, one or more wire clamping mechanisms, one or more linear sliding mechanisms, and can include other components.

The apparatus can further include a driving unit, wherein the first arm is connected to the driving unit that drives the first arm to the longitudinal direction, wherein the breakaway mechanism can include a breakaway connector configured to connect and disconnect the first arm and the second arm, and wherein the second arm is moved to the longitudinal direction while the first arm and the second arm is connected by the breakaway connector and the first arm is driven by the driving unit.

The board can be a blocking board. The at least one positioning sensor can include a sensor configured to detect light that is blocked by the blocking board and determine a home position. The at least one positioning sensor can include a sensor configured to detect light that is blocked by the blocking board and determine a limit position of travel. The blocking board can be configured to provide a negative limit transition and a positive limit and home transition. The blocking board can include a first blocking board and a second blocking board.

The apparatus can further include a controller, wherein in a case where a detection state of the at least one positioning sensor changes from a first state where a blocking of light by the first blocking board is detected to a second state where the blocking of the light by the first blocking board is not detected, the controller determines the tractor is at a home position, and wherein in a case where a detection state of the at least one positioning sensor changes from a third state where a blocking of light by the second blocking board is detected to a fourth state where the blocking of light by the second blocking board is not detected, the controller determines the tractor is at a limit position.

The apparatus can further include a first arm, and a second arm, and a driving unit, wherein the first arm is connected to the driving unit that drives the first arm to the longitudinal direction, wherein the second arm is connected to the wire, and wherein the breakaway mechanism can include a breakaway connector configured to connect and disconnect the first arm and the second arm, wherein the second arm is moved to the longitudinal direction while the first arm and the second arm is connected by the breakaway connector and the first arm is driven by the driving unit.

According to some embodiments, a method can include moving a wire by an actuator along a longitudinal direction, connecting a tractor to the wire to move the wire along the longitudinal direction, connecting a first arm to a driving unit that drives the first arm to the longitudinal direction, connecting the first arm to a board, connecting a second arm to the wire, providing at least one positional sensor configured to detect light from the board, supporting the at least one positional sensor on a support member, and providing a breakaway mechanism that can include a breakaway connector configured to connect and disconnect the first arm and the second arm.

According to some embodiments, a non-transitory storage medium storing a program can cause a computer to execute a method including moving a wire by an actuator along a longitudinal direction, connecting a tractor to the wire to move the wire along the longitudinal direction, connecting a first arm to a driving unit that drives the first arm to the longitudinal direction, connecting the first arm to a board, connecting a second arm to the wire, providing at least one positional sensor configured to detect light from the board, supporting the at least one positional sensor on a support member; and providing a breakaway mechanism that can include breakaway connector configured to connect and disconnect the first arm and the second arm.

According to some embodiments, an apparatus can include an actuator configured to move a wire along a longitudinal direction, a tractor that is connected to the wire and is configured to move the wire along the longitudinal direction, a board that can include at least a first channel and a second channel, and a plurality of sensors that can include at least a first sensor and a second sensor arranged at a different position from each other along a direction perpendicular to the longitudinal direction, wherein the first sensor is configured to determine a home position, and wherein the second sensor configured to determine a limit position of travel based on emitted light.

The first channel and the second channel of the board each have a length, wherein the length of the first channel is shorter than the length of the second channel. The first channel and the second channel of the board can be configured to move along with movement of the tractor.

The board can be a blocking board. The first sensor can include a home positioning sensor configured to detect light that is blocked by the blocking board and determine a home position. The second sensor can include a traveling limitation sensor configured to detect light that is blocked by the blocking board and determine a limit position of travel. The blocking board can be configured to provide a negative limit transition and a positive limit and home transition. The blocking board can include a first blocking board and a second blocking board.

The apparatus can further include a controller, wherein in a case where a detection state of the first sensor changes from a first state where a blocking of light by the first blocking board is detected to a second state where the blocking of the light by the first blocking board is not detected, the controller determines the tractor is at a home position, and wherein in a case where a detection state of the second sensor changes from a third state where a blocking of light by the second blocking board is detected to a fourth state where the blocking of light by the second blocking board is not detected, the controller determines the tractor is at a limit position.

The board can be a reflective board. The first sensor can include a home positioning sensor and the first sensor can include a home positioning sensor configured to detect reflection light from the reflective board and determine a home position. The second sensor can include a traveling limitation sensor configured to detect reflection light from the reflective board and determine a limit position of travel. The reflective board can be configured to provide a negative limit transition and a positive limit and home transition. The reflective board can include a first reflective board and a second reflective board.

The apparatus can further include a controller, wherein in a case where a detection state of the first sensor changes from a first state where a reflection from the first reflective board is detected to a second state where the reflection from the first reflective board is not detected, the controller determines the tractor is at a home position, and wherein in a case where a detection state of the second sensor changes from a third state where a reflection from the second reflective board is detected to a fourth state where the reflection from the second reflective board is not detected, the controller determines the tractor is at a limit position.

The wire can include a plurality of wires. The apparatus can include one or more force sensors configured to measure push and pull forces on the wire, one or more wire clamping mechanisms, one or more linear sliding mechanisms, and can include other components.

The apparatus can include a breakaway mechanism configured to disconnect the actuator and the tractor in a case where an applied force is greater than a predetermined value. The breakaway mechanism can include a breakaway sensor configured to detect when breakaway occurs. In a case where breakaway detected by the breakaway sensor, a recovery and homing routine can be initiated, and/or an error state can be initiated that can prompt a service technician or other to diagnose the apparatus. The breakaway mechanism can be configured to return the tractor to home position in a case where breakaway occurs.

The apparatus can further include a first arm, and a second arm, and a driving unit, wherein the first arm is connected to the driving unit that drives the first arm to the longitudinal direction, wherein the second arm is connected to the wire, and wherein the breakaway mechanism can include a breakaway connector configured to connect and disconnect the first arm and the second arm, wherein the second arm is moved to the longitudinal direction while the first arm and the second arm is connected by the breakaway connector and the first arm is driven by the driving unit.

According to some embodiments, a method can include moving a wire by an actuator along a longitudinal direction, connecting a tractor to the wire to move the wire along the longitudinal direction, providing a board that can include at least a first channel and a second channel, providing a plurality of sensors that can include at least a first sensor and a second sensor, arranging the first sensor and the second sensor at a different position from each other along a direction perpendicular to the longitudinal direction, causing the first sensor to determine a home position based on emitted light, and causing the second sensor to determine a limit position of travel based on emitted light.

According to some embodiments, a non-transitory storage medium storing a program can cause a computer to execute a method including moving a wire by an actuator along a longitudinal direction, connecting a tractor to the wire to move the wire along the longitudinal direction, providing a board that can include a first channel and a second channel, providing a plurality of sensors that can include at least a first sensor and a second sensor, arranging the first sensor and the second sensor at a different position from each other along a direction perpendicular to the longitudinal direction, causing the first sensor to determine a home position, and causing the second sensor to determine a limit position of travel based on emitted light.

These and other objects, features, and advantages of the present disclosure will become apparent upon reading the following detailed description of exemplary embodiments of the present disclosure, when taken in conjunction with the appended drawings, and provided claims.

Further features of the present disclosure will become apparent from the following description of exemplary embodiments with reference to the attached drawings, where like structure is indicated with like reference numerals.

BRIEF DESCRIPTION OF THE DRAWINGS

FIG. 2 illustrates an operational diagram of the homing channel with a blocking surface according to some embodiments.

FIG. 6 is an operational diagram of the home sensor and the limiting sensor with a reflective board according to some embodiments.

FIG. 8 illustrates an operational diagram of the limit channel with a reflective surface according to some embodiments.

FIG. 13 is a block diagram of a controller according to some embodiments.

FIG. 26 is a flow chart of a method of moving a wire with a reflective board according to some embodiments.

DESCRIPTION OF THE EMBODIMENTS

Figure 1:
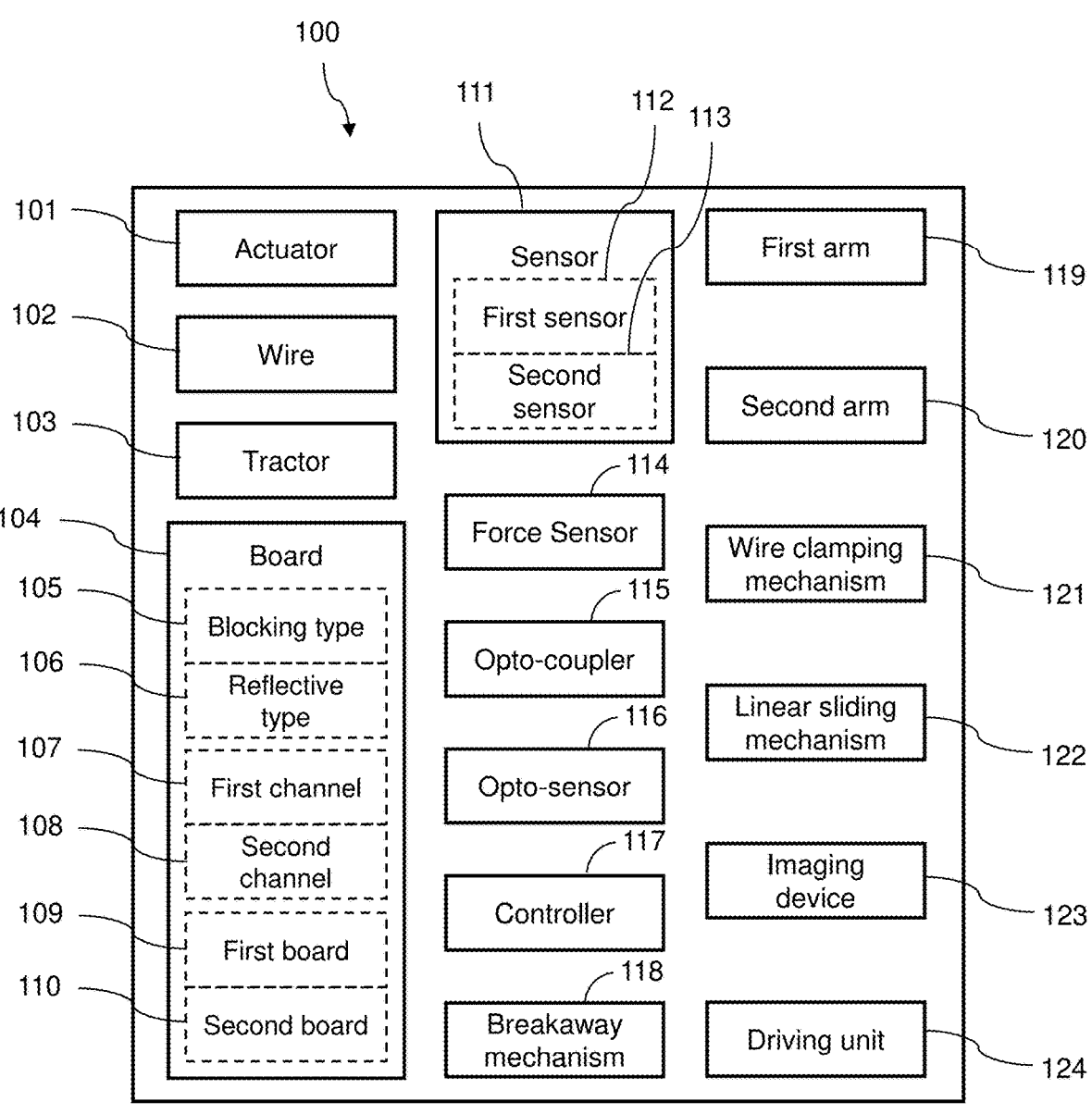
FIG. 1 is a block diagram of an exemplary apparatus for position sensing using various combinations of optical sensors, couplers, reflective boards, blocking boards, breakaway mechanisms, and other components according to some embodiments.

Various exemplary embodiments, features, and aspects of the disclosure that relate to apparatuses, methods, storage mediums, and other configurations to re-engage breakaway and integrate homing control and travel limiting control will be described below with reference to the drawings that may have different characteristics, advantages, disadvantages, performance parameters, or the like.

The present disclosure advantageously provides solutions to re-engage breakaway and to integrate homing control and travel limiting control together to prevent the chance of a tractor experience in a crash situation where the tractor gets jammed.

Some embodiments are directed to apparatuses, methods, and mediums for position sensing using various combinations of sensors, couplers, reflective boards, blocking boards, breakaway mechanisms, and other components.

Some embodiments functionally implement breakaway re-engagement and homing control and travel limiting control integration in medical, non-medical, industrial, automotive, logistics, agriculture, or other areas to increase accuracy of device or component positional detection, measurement, movement, or the like.

Some embodiments functionally implement continuum robot, snake robot, snake robotic assembly, snake endoscopic assembly, snake robotic catheter assembly, or other arrangements or configurations that can implement a flexible device to carry out medical procedures including imaging, diagnostic, endoscopic, biopsy, therapeutic, surgical, image guided therapy, or other procedures. Endoscopic procedures include colonoscopy (bowel), gastroscopy (stomach), cystoscopy (bladder), bronchoscopy (airways of the lung), laparoscopy (abdomen), and other types of procedures.

Some embodiments functionally implement imaging modalities including CT (computed tomography), MRI (magnetic resonance imaging), IVUS (intravascular ultrasound), PET (positron emission tomography), X-ray imaging, optical coherence tomography (OCT), swept source OCT (SS-OCT), spectral domain OCT (SD OCT), optical frequency domain imaging (OFDI), Fourier domain OCT (FD-OCT), time domain OCT (TD-OCT), multi-modality OCT (MMOCT), spectrally encoded endoscopy (SEE), other imaging modalities, combinations or hybrids thereof. Arrangements can also functionally implement light detection and ranging (LiDAR) configurations that are used to measure distances to remote targets. The present disclosure is not limited to any particular configuration.

SD OCT is an OCT technique of acquiring the spectral distribution of the interference light by time division, and SD OCT is an OCT technique of acquiring the spectral distribution of the interference light by space division.

In continuum robot or snake robotic configurational embodiments, for example, a flexible device such as a catheter, endoscope, or the like, can be controlled to navigate, insert, retract, roll, articulate, or combinations thereof based on inputs received manually, semi-automatically, automatically or combinations thereof. Flexible devices can include one or more wires or wire configurations including control wires, operation wires, drive wires, push wires, pull wires, push-pull wires, wire bundles, tendons, tendon wires, other wire configurations, or combinations thereof.

Controllable actuators can adjust the wires to adjust portions including the distal tip of the flexible device in any geometric or angular direction, e.g., up, down, left, right, translationally, rotationally, or combinations thereof.

FIG. 1 illustrates an exemplary hardware configuration of an apparatus 100 to re-engage breakaway and integrate homing control and travel limiting control according to some embodiments.

The apparatus 100 includes one or more of an actuator 101, a wire 102, a tractor 103, a board 103, a sensor 111, a force sensor 114, an opto-coupler 115, an opto-sensor 116, a controller 117, a breakaway mechanism 118, a first arm 119, a second arm 120, a wire clamping mechanism 121, a linear sliding mechanism 122, an imaging device 123, a driving unit 124, and can include other components or combinations thereof.

The actuator 101 is configured to move the wire 102 along a longitudinal direction. The actuator 101 includes one or more motors and can drive components of the apparatus 100. The tractor 103 can be connected to the wire 102 and can be configured to move the wire 102 along the longitudinal direction. The tractor 103 can be attachably and detachably connected to the first arm 119 and the second arm 120. The wire 102 can include a plurality of wires or wire bundles.

The board 104 can be configured as a blocking board type 105, a reflective board type 106, another board type, or combinations thereof. The board 104 can be configured with one or more channels including a first channel 107, a second channel 108, and can include other channels. The board 104 can be configured with one or more boards including a first board 109, a second board 110, and can include other boards.

In other words, the board 104 can be a blocking board 105, a reflective board 105, another board type, or combinations thereof, and can each have a plurality of channels and a plurality of boards. Throughout the present disclosure, reference to 'a board' can refer to one or more blocking boards, one or more reflective boards, one or more other boards, or combinations thereof. Some embodiments of the present disclosure can use various combinations of blocking boards, reflective boards, or combinations thereof. There are no limitations to the number of boards.

One or more sensors 111 can be associated with the board 104. For example, a home positioning sensor and a travel limitation sensor can be arranged on a sensor board, and the board 104 can be used in various configurations to carry out a homing routine and/or a travel limiting routine, as will be described below.

In a case where the board 104 is the blocking board 105, a first sensor 112 can include a home positioning sensor configured to determine a home position based on emitted light. For example, the first sensor 112 can detect light that is blocked by the blocking board type 105 and determine a home position. A second sensor 113 can include a traveling limitation sensor configured to determine a limit position of travel. For example, the second sensor 113 can detect light that is blocked by the blocking board type 105 and determine a limit position of travel. The blocking board type 105 can be configured to provide a negative limit transition and a positive limit and home transition. The blocking board type 105 can include a first board 109 and a second board 110.

In a case where the board 104 is the reflective board type 106, the first sensor 112 can include a home positioning sensor determine a home position based on emitted light. For example, the first sensor 112 can detect emitted light in the form of reflection light from the reflective board type 106 and determine a home position. The second sensor 113 can include a traveling limitation sensor configured to determine a limit position based on emitted light. For example, the second sensor 113 can detect the reflection light from the reflective board type 106 and determine a limit position of travel. The reflective board type 106 can be configured to provide a negative limit transition and a positive limit and home transition. The reflective board type 106 can include a first board 109 and a second board 110.

In a case where the board 104 is the blocking board type 105 and one or more blocking boards type 105 are used with a first channel 107 and a second channel 108, FIG. 2 illustrates the first channel 107 of the blocking board type 105 configured as a homing channel. For the homing channel, an opto-coupler or optical coupler can be used and can include an emitter, a collector, a blocking surface or blocking board, and can include other elements or combinations thereof. In FIG. 2, the opto-coupler components are arranged as a blocking opto-senor configuration, where the emitter and collector are facing each other and the introduction of the blocking surface disrupts the signal. When the homing channel operates in State A, a high signal tells the tractor 103 to move in a positive direction to find zero. When the homing channel operates in State B, a low signal tells the tractor 103 to move in a negative direction to find zero. The positive direction is shown to the right (+) and the negative direction is shown to the left (−).

The homing channel (the first channel) may contain an opaque surface, where the sensor will be triggered 'ON' for State A and triggered 'OFF' for State B. A homing routine may be engaged in an on signal (State A) and will tell the actuator 101 to move the tractor 103 in toward the positive direction (for example, to the direction that the first arm 119 is pushed) until the state is triggered off. This will indicate that the tractor 103 has reached the home position. Similarly, if the homing routine is enabled in an off state (State B), the tractor 103 will move in the opposite direction (for example, to the distance past the home position and return the other way until the sensor 110 is triggered again. This will account for hysteresis error in the sensor 111 and allow for better homing accuracy, e.g., unidirectional homing.

Figure 3:
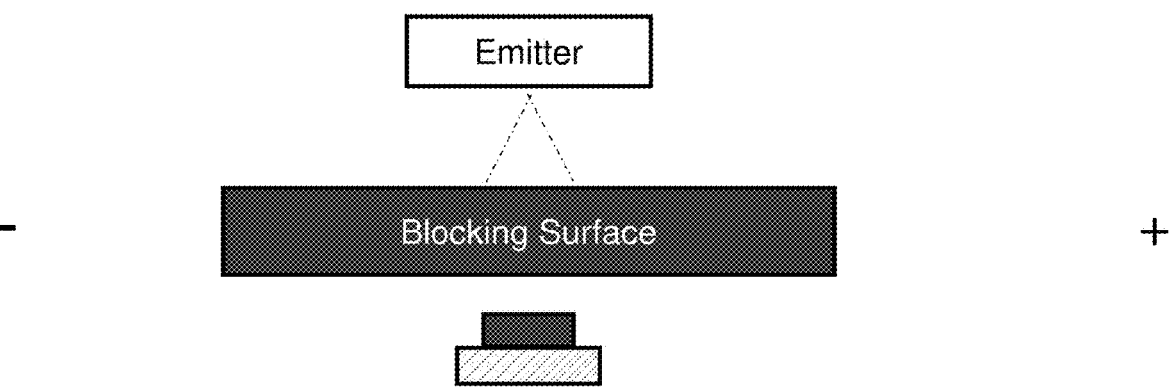
FIG. 3 illustrates an operational diagram of the limit channel with a blocking surface according to some embodiments.

FIG. 3 illustrates the second channel 108 configured as a limit channel. The limit channel is used for detecting the end of travel to prevent tractor collision and jamming. In the limit channel, the blocking surface blocks the emitter from the reflector. With a combination of both limit and home channels, the apparatus 100 can now detect both the limit position of travel and which limit is positive or negative. Without the homing channel, the apparatus 100 would know if it reached a limit, but would not know which limit and therefore would not know with direction to move.

Figure 4:
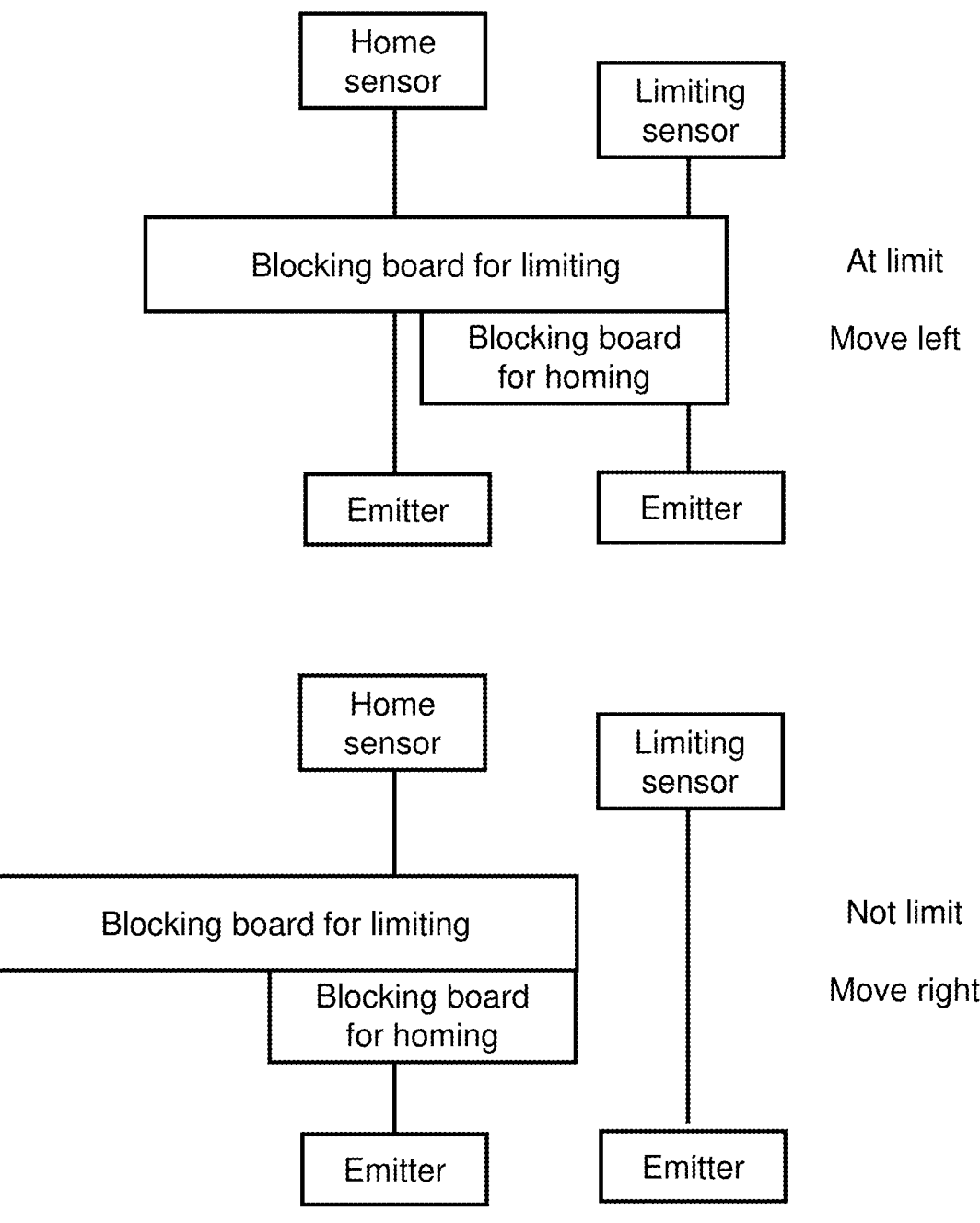
FIGS. 4 and 5 are operational diagrams of the home sensor and the limiting sensor with blocking boards according to some embodiments.

FIG. 4 illustrates operational movement when there are two blocking boards including a blocking board for homing and a blocking board for limiting. In a case where the homing and limiting boards are at the limit, the boards can move to the left. In a case where the homing and limit boards are not at the limit, the boards can move to the right.

Figure 5:
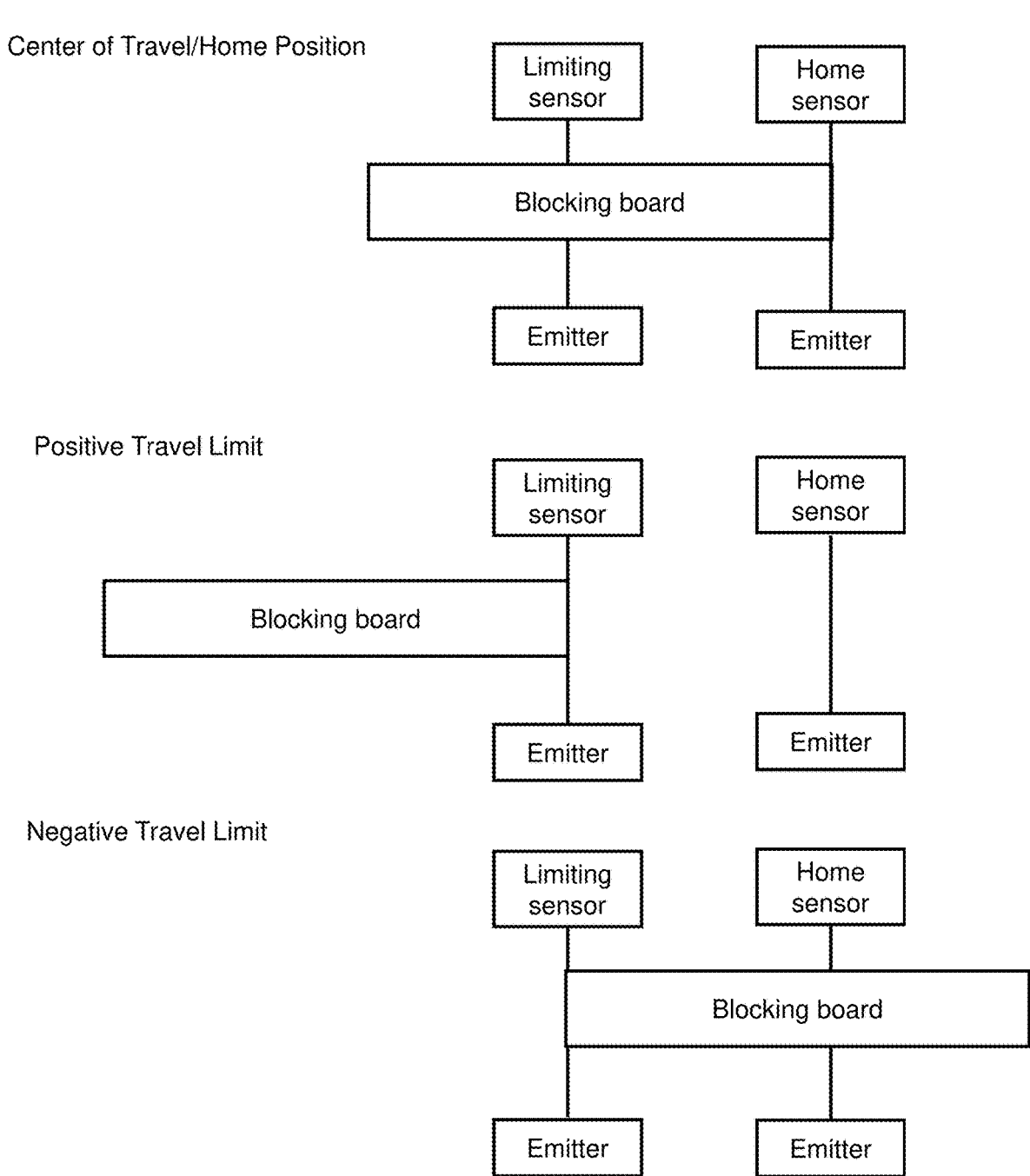

For a blocking board configuration, FIG. 5 illustrates operational movement for a travel limit sensor where a limit and home sensors are blocking opto-senor configurations, where the emitter and collector are facing each other and the introduction of the blocking surface disrupts the signal. The blocking board position at the center of travel or home position are shown at the top of FIG. 5, the blocking board position at the positive travel limit is shown in the center of FIG. 5, and the blocking board position at the negative travel limit is shown at the bottom of FIG. 5. When the homing channel operates in State A, a high signal tells the tractor 103 to move in a positive direction to find zero. When the homing channel operates in State B, a low signal tells the tractor 103 to move in a negative direction to find zero. The positive direction is shown to the right (+) and the negative direction is shown to the left (−).

In a case where one or more reflective board types 106 are used with a first channel and a second channel, FIG. 6 illustrates the first channel 107 configured as a homing channel. When the homing channel operates in State A, a high signal tells the tractor 103 to move in a positive direction to find zero. When the homing channel operates in State B, a low signal tells the tractor 103 to move in a negative direction to find zero.

The homing channel (the first channel 107) may contain a reflective surface for only one half of travel, where the sensor 110 will be triggered 'ON' for the first half of travel and 'OFF' for the second half. A homing routine may be engaged in an on signal (State A) and will tell the actuator 101 to move the tractor 103 in toward the positive direction (for example, to the direction that the first arm 119 is pushed) until the state is triggered off. This will indicate that the tractor 103 has reached the home position. Similarly, if the homing routine is enabled in an off state (State B), the tractor 103 will move in the opposite direction (for example, to the distance past the home position and return the other way until the sensor 110 is triggered again. This will account for hysteresis error in the sensor 111 and allow for better homing accuracy, e.g., unidirectional homing.

The home position is not necessarily at the center or a half of the travel. The home position can be located anywhere in the travel of the first arm 119 and the length of the first channel 107 of the reflective board can be determined in accordance with the position of the home position.

Figure 7:
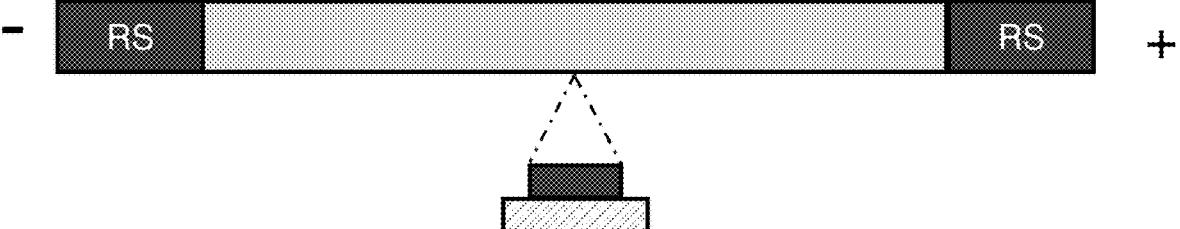
FIG. 7 illustrates an operational diagram of the homing channel with a reflective surface according to some embodiments.

FIG. 7 illustrates the second channel 108 configured as a limit channel. The limit channel is used for detecting the end of travel to prevent tractor collision and jamming. In the limit channel, the reflective surface RS in the center drops off on both edges of travel before the end of travel hard stop is hit. With a combination of both limit and home channels, the apparatus 100 can now detect both the limit position of travel and which limit is positive or negative. Without the homing channel, the apparatus 100 would know if it reached a limit, but would not know which limit and therefore would not know with direction to move.

For a reflective board configuration, FIG. 8 illustrates operational movement for a travel limit sensor where a limit and home sensors are reflective board type configurations. The reflective board position at the center of travel or home position are shown at the top of FIG. 8, the reflective board position at the positive travel limit is shown in the center of FIG. 8, and the reflective board position at the negative travel limit is shown at the bottom of FIG. 8. When the homing channel operates in State A, a high signal tells the tractor 103 to move in a positive direction to find zero. When the homing channel operates in State B, a low signal tells the tractor 103 to move in a negative direction to find zero. The positive direction is shown to the right (+) and the negative direction is shown to the left (−).

The sensor 111 is configured with one or more sensors including a first sensor 112, a second sensor 113, and can include other sensors. The sensor 111 is configured to detect or respond to physical or environmental changes and convert them into measurable signals or data. The sensor 110 can gather information about various parameters of the apparatus 100 including position, motion, proximity, light, temperature, force, pressure, humidity, other parameters. The sensor 111 can be configured as a light-based sensor, an opto-sensor, an optical sensor, a photocell, a photoelectric sensor, an electrical-field based sensor, a capacitive or inductive proximity sensor, or other types of sensors, or combinations thereof.

The first sensor 112 can be a home positioning sensor configured to detect reflection light from the reflective board type 106 and determine a home position, and the second sensor 113 can be a traveling limitation sensor configured to detect reflection light from the reflective board type 106 and determine a limit position of travel. Additionally, the state of the first sensor 112 or home positioning sensor can determine whether the limit is a positive or negative end.

The force sensor 114 is configured to measure push and pull forces on the wire, and can detect translational force or movement in the X-axis, Y-axis, Z-axis, and separately detect rotational force or motion around a yaw-axis, a pitch-axis, roll-axis, or other directions. The force sensor 114 can include an opto-sensor, force/torque sensor, or other type of sensor, that enables the apparatus to respond electromechanically to movement of the wire 102.

The opto-coupler 115 or optical coupler can include an emitter, a collector, a blocking board, a reflective board, and can include other elements, or combinations thereof. The opto-coupler 115 is configured for use where light is transmitted from the emitter to the collector. The emitter is a light emitting element which transforms an electrical signal to an optical signal. The collector is a light receiving element which transforms the optical signal to an electrical signal.

The opto-coupler 115 works with opto-sensors that detect presence, length, number, or other attributes of objects, using visible or infrared light which is blocked or reflected by the object. The continuity or disruption of this signal allows for sensing. The opto-coupler 115 components can be arranged as opto-sensor configurations including a reflective opto-sensor, a blocking opto-sensor, or other types of opto-sensors.

Figure 9:
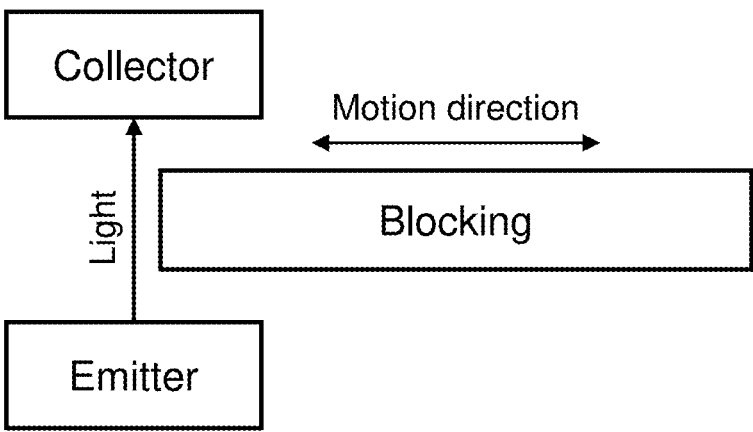
FIG. 9 illustrates an operational diagram of a blocking opto-sensor according to some embodiments.
Figure 10:
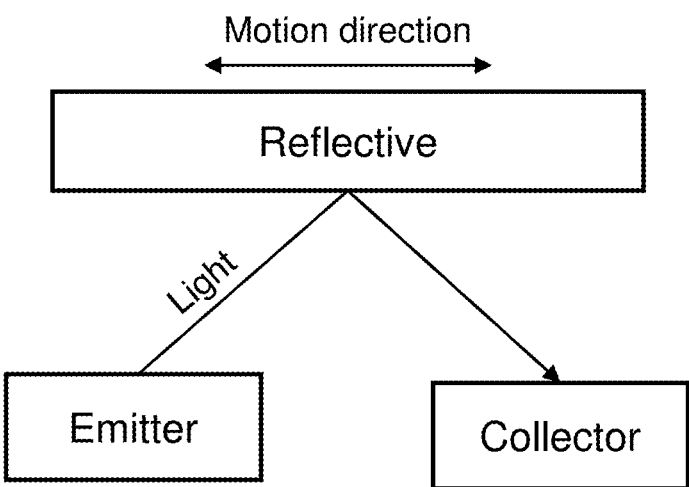
FIG. 10 illustrates an operational diagram of a reflective opto-sensor according to some embodiments.

In FIG. 9, the opto-coupler 115 components are arranged as a blocking opto-senor configuration, where the emitter and collector are facing each other and the introduction of the blocking surface disrupts the signal. In FIG. 10, the opto-coupler 115 components are arranged as a reflective opto-sensor configuration, where the collector and emitter are planar and the light reflects off a surface to complete the circuit.

The opto-sensor or optical sensor 116 can include an electro-optical device configured to transform applied forces and/or torques into electrical signals, thereby enabling a desired force/torque input to be sensed and transformed into a motion that is provided in the sensed linear and/or rotational direction(s). The apparatus 100 can use other types of sensors including a strain gauge, piezoelectric device, or other types of sensors.

While blocking type and reflective type sensor configurations serve the same function there may be more advantageous for a given design. With the blocking sensor type the path between the emitter and the collector may be better contained, shielding the signal from external noise. There should not be any concern about selecting special material, as long as the material is opaque enough to block the light. Alignment is also less of an issue with a blocking type sensor as the emitter and collector can be contained in a monolithic housing that is generally aligned by the manufacturer. A difficulty with a blocking sensor can be that the emitter and collector may be located in different planes which take up multiple space. The blocking board may also be a component designed in a particular manner with a thin surface with the slides positioned between the emitter and collector (without interfering with the sensor).

For some embodiments, the blocking sensor is preferable due to the advantages listed above, as the volumetric constraints should not be an issue and the blocking type may be less susceptible to error.

The reflective type sensor works well for a design that has strict volume criteria as the emitter and collector are on the same face/plane creating a compact profile. The reflective board can be an existing component (i.e., the face of the tractor). A difficulty with the reflective sensor may be proper alignment and material selection. If the material is not reflective enough, or the alignment is off there is a higher chance of not receiving a signal to the collector. Also, since the collector may be more exposed, there is the chance for other light generating a false signal, or the emitter light reflecting off another surface, triggering the sensor incorrectly.

According to some embodiments, combinations of blocking boards or reflective boards with sensors as described above or other sensors, such as photosensors or the like, can be used for position sensing. In a case where a blocking board is used, sensors such as photosensors or the like can detect blocking of light by the blocking board. In a case where a reflective board is used, sensors such as photosensors or the like can detect reflection light from the reflective board. Phraseology similar to these can be interchanged depending on whether a blocking board or a reflective board is being used.

For example, in a case where a blocking board is used instead of a reflective board for the position sensing, "photosensors detect reflection from the reflection board" in the embodiments can be replaced with "photosensors detect blocking of light by the blocking board" and "photosensors do not detect the reflection from the reflective board" in the embodiments can be replaced with "photosensors do not detect blocking of light by the blocking board."

The controller 117 includes at least one processor, circuitry, or combinations thereof and is configured to control all elements of the apparatus 100. The first arm 119 can be attachably and detachably connected to or removably attachable to the second arm 120 by the breakaway mechanism 118. The breakaway mechanism 118 is configured to disconnect the actuator 101 and the tractor 103 in a case where an applied force is greater than a predetermined value. For example, the breakaway mechanism can disconnect the first arm 119 from the second arm 120 in a case where an applied force is greater than a predetermined value. The breakaway mechanism 118 is configured to return the tractor 103 to a home position in a case where breakaway occurs. The breakaway mechanism 118 can be configured with a breakaway sensor that can detect when breakaway occurs. In a case where breakaway occurs and is detected by the breakaway sensor, a recovery and homing routine can be initiated, and/or an error state can be initiated that can prompt a service technician or other to diagnose the apparatus 1000.

The first arm 119 and the second arm 120 are configured to slide on the linear sliding mechanism 122. The imaging device 123 can be mechanical, digital, electrical, or combinations thereof, and is configured to record, store, or transmit visual images. The driving unit 124 can include one or more motors and can operate in connection with the actuator 101.

Figure 11:
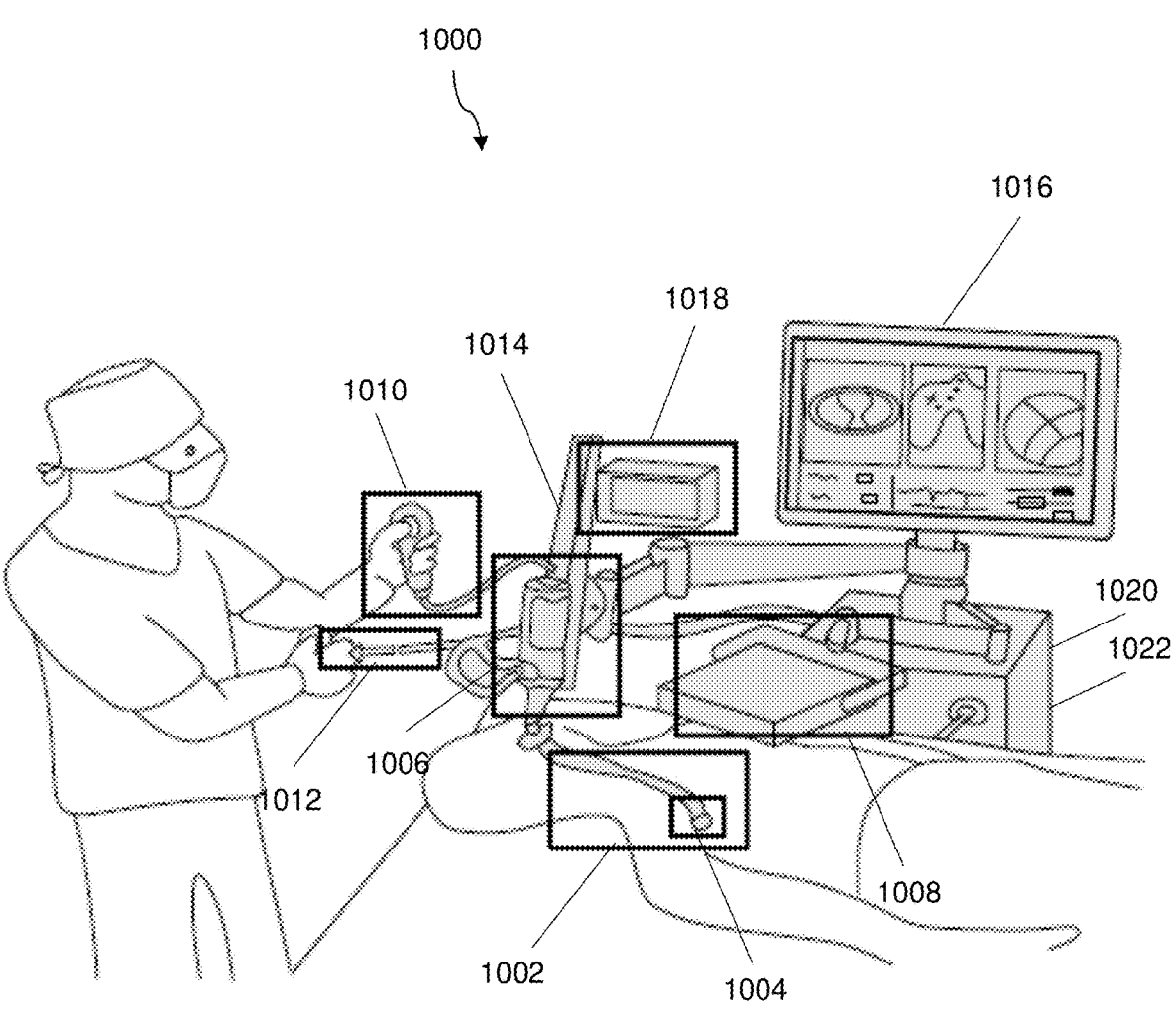
FIG. 11 illustrates an exemplary apparatus for position sensing using various combinations of optical sensors, couplers, reflective boards, blocking boards, breakaway mechanisms, and other components according to some embodiments.
Figure 12:
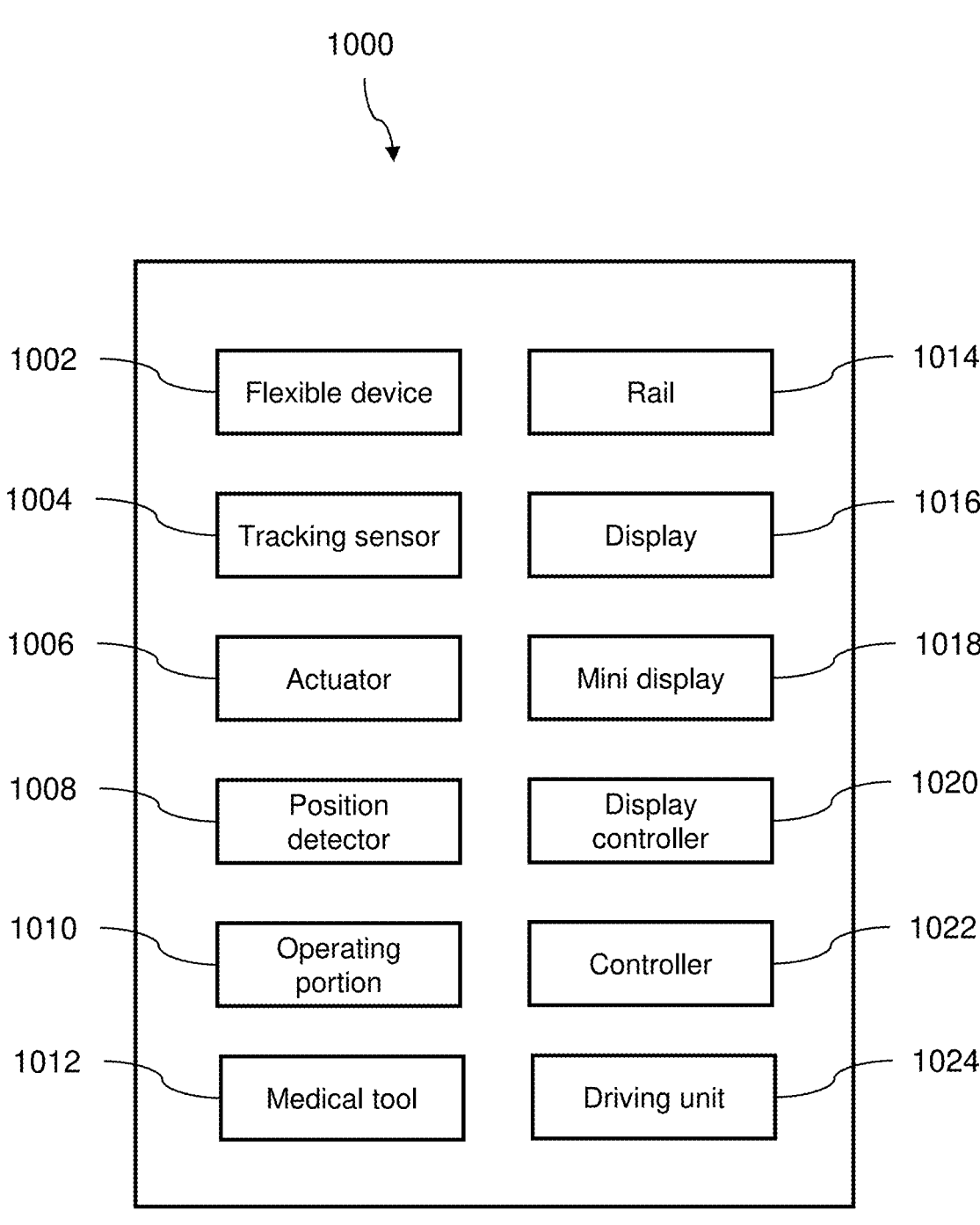
FIG. 12 is a block diagram of the apparatus of FIG. 11 according to some embodiments.

FIG. 11 illustrates an exemplary apparatus or configuration 1000 to re-engage breakaway and integrate homing control and travel limiting control according to some embodiments. FIG. 12 shows a hardware configuration of the apparatus 1000.

The apparatus 1000 includes one or more of a flexible device 1002, a tracking sensor 1004, an actuator 1006, a position detector 1008, an operating portion or manipulator 1010, a medical tool 1012, a rail 1014, a display 1016, a mini display 1018, a display controller 1020, a controller 1022, a driving unit 1024, and can include other components. The apparatus 1000 can include any of the components of the apparatus 100 of FIG. 1.

The flexible device 1002 is configured to examine or treat an area in an object, such as a patient or the like. The tracking sensor 1004 detects movement of the tip of the flexible device 1002. The actuator 1006 includes one or more motors and can drive components of the apparatus 1000. The position detector 1008 detects a position of the tracking sensor 1004, which can be an electro-magnetic (EM) tracking sensor or another type of sensor, that is mounted on the tip of the flexible device 1002 and outputs the detected positional information to the controller 1022. The operating portion or manipulator 1010 is configured to move the flexible device 1002 based on input commands. The medical tool 1012 can be a biopsy tool or other type of tool. The rail 1014 supports the flexible device 1002 and medical tool 1012 so they can move along the rail 1014. The display 1016 and the mini display 1018 each display operational information about the apparatus 1000 including informational and analytical data, medical information, medical imagery, captured images, captured moving images, or other types of information. The display controller 1020 controls the display 1016 and the mini display 1018. The controller 1022 controls the elements of the apparatus 1000. The driving unit 1024 includes one or more motors and operates in connection with the actuator 1006.

The flexible device 1002 can be a flexible, steerable, or elongate tool, instrument, or other device, e.g., continuum robot, snake robot, snake robotic assembly, snake endoscopic assembly, snake robotic catheter assembly, catheter, endoscope, colonoscope, bronchoscope, ablation device, guide wire, or other device, and may be configured to be long and thin to look inside an object, where an instrument is passed through the tool to examine or treat an area in the object, such as a patient or the like. The flexible device 1002 may be configured to be long and thin.

The EM tracking sensor 1004 is attached to and detects movement of the tip of the flexible device 1002. The actuator 1006 can include a rotational drive assembly and is releasably connected to the flexible device 1002, and is configured to impart translational, rotational, or other type of movement to the flexible device 1002. The position detector 1008 detects a position of the EM tracking sensor 1006 at the tip of the flexible device 1002 and outputs the detected positional information to the controller 1022.

The operating portion or manipulator 1010 has a housing with an elongated handle or handle section which can be manually grasped, and one or more input devices including, for example, a lever or a button or another input device that allows an operator, such as a physician, nurse, technician, or the like, to send a command to the apparatus 1000 to move the flexible device 1002. The controller 1022 executes software, computer instructions, algorithms, or the like, so the user can complete all operations with the hand-held operating portion 1010 by holding it with one hand.

The controller 1022 receives the positional information of the flexible device tip directly from the tracking sensor 1004 or from the detector 1008. The flexible device 1002 can include an imaging device that is mechanical, digital, electronic, or combinations thereof, to record, store, or transmit visual images, e.g., a camera, camcorder, motion picture camera, or the like.

The medical tool 1012 can be a biopsy tool or other type of tool. The actuator 1006 can include one or more motors and can drive each section of the flexible device 1002. The flexible device 1002 and medical tool 1012 are movably supported on the rail 1014. The controller 1022, flexible device 1002, tracking sensor 1004, and other elements are interconnected to the actuator 1006. The controller 1022 includes at least one processor, circuitry, or combinations thereof, and is configured to control all elements of the apparatus 1000 including the medical tool 1012 through the actuator 1006, and to control the actuator 1006 in accordance with the manipulation by the user, semi-automatically, automatically, or combinations thereof.

The driving unit 1024 can include one or more motors and can operate in connection with the actuator 1006.

The display 1016 and the mini display 1018 may be a display device configured, for example, as a monitor, an LCD (liquid-crystal display), an LED (light-emitting diode) display, an OLED (organic LED) display, a plasma display, an organic electro luminescence panel, or the like. The display controller 1020 controls the display 1016 and the mini display 1018. Based on the control of the apparatus 1000, a navigation screen may be displayed on the display 1016, 1018 showing one or more images being captured, captured images, captured moving images recorded on the storage unit, or the like.

The controller 1022 operates to control the elements of the apparatus 1000 and has one or more configurational components that include, as shown in FIG. 13, one or more of a processor 1031, a memory 1032, a sensor 1033, an input and output (I/O) interface 1034, a communication interface 1035, communication interface 1035, a display or graphical user interface (GUI) 1036, a power source 1037, and can include other components. The apparatus 1000 can be interconnected with medical instruments or a variety of other devices, and can be controlled independently, externally, or remotely by the controller 1022.

The processor 1031 can be configured as a control circuit, circuitry, or combinations thereof (central processing unit (CPU), micro processing unit (MPU), or the like), for performing overall control of the apparatus 1000, and can execute a program, instructions, code or software stored in the memory 1032 to perform various data processing, computation, algorithmic tasks, or other functions of the apparatus 1000. The memory 1032 can store the program, software, computer instructions, information, other data, or combinations thereof. The memory 1032 is used as a work memory. The processor 1031 executes the software developed in the memory 1032. The I/O interface 1034 inputs the catheter positional information to the controller 1022 and outputs information for displaying the navigation screen to the display 1038. The power source 1037 provides regulated power supply to the apparatus 1000, and can include an external power source such as line power or AC power from a power outlet that can interconnect with the apparatus 1000 through an AC/DC adapter and a DC/DC converter, or an AC/DC converter in order to adapt the power voltage from a source into one or more voltages used by components in the apparatus 1000.

The components are connected together by a bus 1038 so that the components can communicate with each other. The bus 1038 transmits and receives data between these pieces of hardware connected together, or transmits a command from the processor 1031 to the other pieces of hardware. The components can be implemented by one or more physical devices that may be coupled to the processor 1031 through the communication interface 1035 to a communication channel. For example, the controller 1022 can be implemented using circuitry in the form of ASIC (application specific integrated circuits) or the like. Alternatively, the controller 1022 can be implemented as a combination of hardware and software, where the software is loaded into a processor from a memory or over a network connection. Functionality of the controller 1022 can be stored on a storage medium, which may include random-access memory (RAM), read only memory (ROM), magnetic or optical drive, diskette, cloud storage, or the like.

Figure 14:
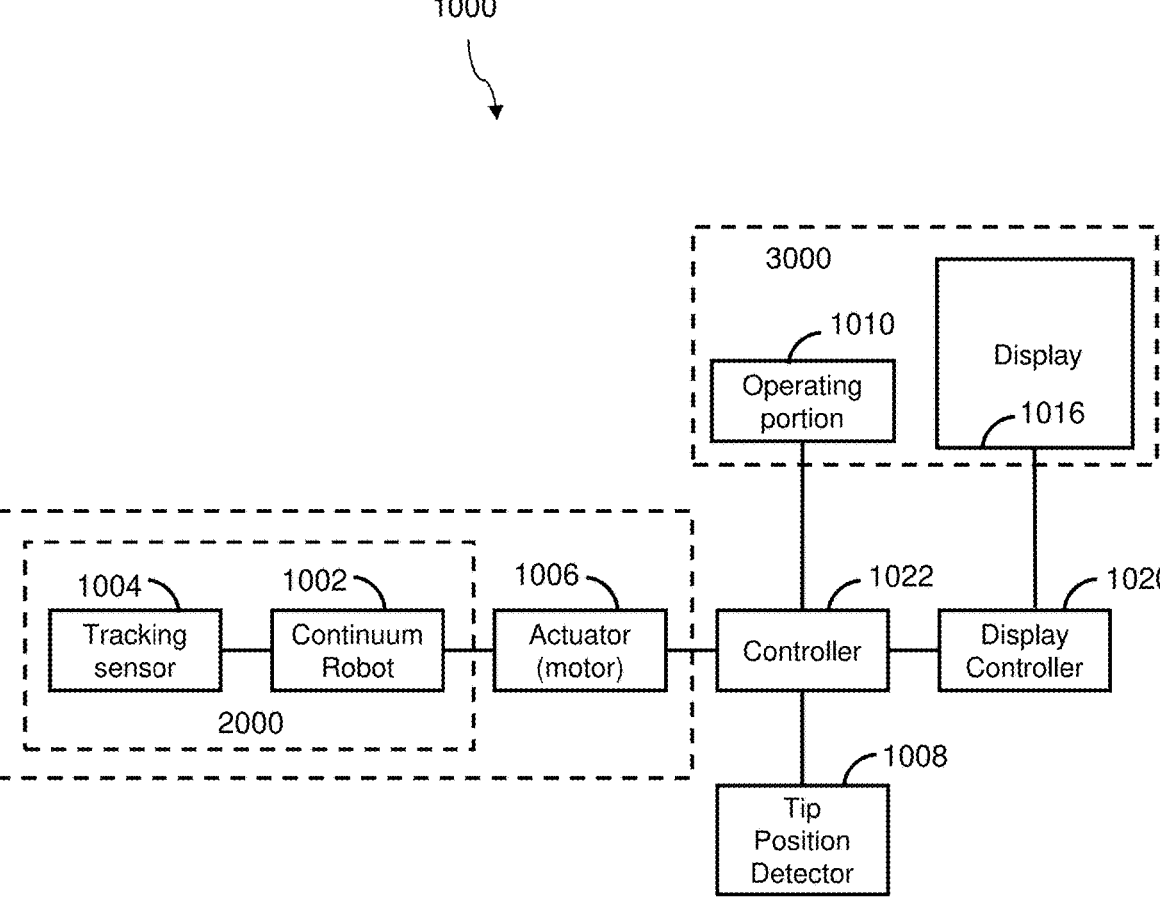
FIG. 14 is an operational block diagram of the apparatus of FIG. 6 according to some embodiments.

FIG. 14 shows an operational configuration of the apparatus 1000 where the flexible device 1002 is configured as a continuum robot that can include a catheter device. The apparatus 1000 includes an operating device 2000 and a receiving device 3000. The operating device 2000 includes continuum robot 1002 and the tracking sensor 1004. The receiving device 3000 includes the operating portion 1010 and the display 1016 and can include the mini display 1018. The EM tracking 1004 is attached to the tip of the continuum robot 1002. The tip position detector 1008 detects a position of the EM tracking sensor 1004 and outputs the detected positional information to the controller 1022.

The continuum robot 1002 can be attachable/detachable to the actuator 1006 and the continuum robot 1002 can be disposable. The display controller 1020 executes a software program and controls to display a navigation screen of the continuum robot 1002 on one or more of the displays 1016, 1018. The display controller 1020 acquires position information of the continuum robot 1002 from the controller 1022. Alternatively, the display controller 1020 may acquire the position information directory from the tip of the continuum robot 1004 via the tip position detector 1008.

The controller 1022 receives the positional information of the tip of the continuum robot 1004 from the tip position detector 1008. The controller 1022 controls the actuator 1006 in accordance with the manipulation by a user via one or more operation portion 1010. The one or more displays 1016, 1018 and/or operation portion 1010 are used as a user interface 3000 (receiving device). In this embodiment, the apparatus 1000 includes, as the user interface 3000 or an operation unit, display 1016 (a large screen user interface with a touch panel, first user interface unit), mini display 1018 (a compact user interface with a touch panel, second user interface unit) and operating portion 1010 (a joystick shaped user interface unit having shift lever/button, third user interface unit).

The controller 1022 and the display controller 1020 can be configured separately. The controller 1022 may include a processor, circuitry, or combinations thereof, a central processing unit (CPU), random access memory (RAM), input/output interface (I/O), read only memory (ROM), hard disk drive (HDD), and can include other components. Alternatively, the controller 1022 and the display controller 1020 can be configured as one device.

Figures 15A, 15B:
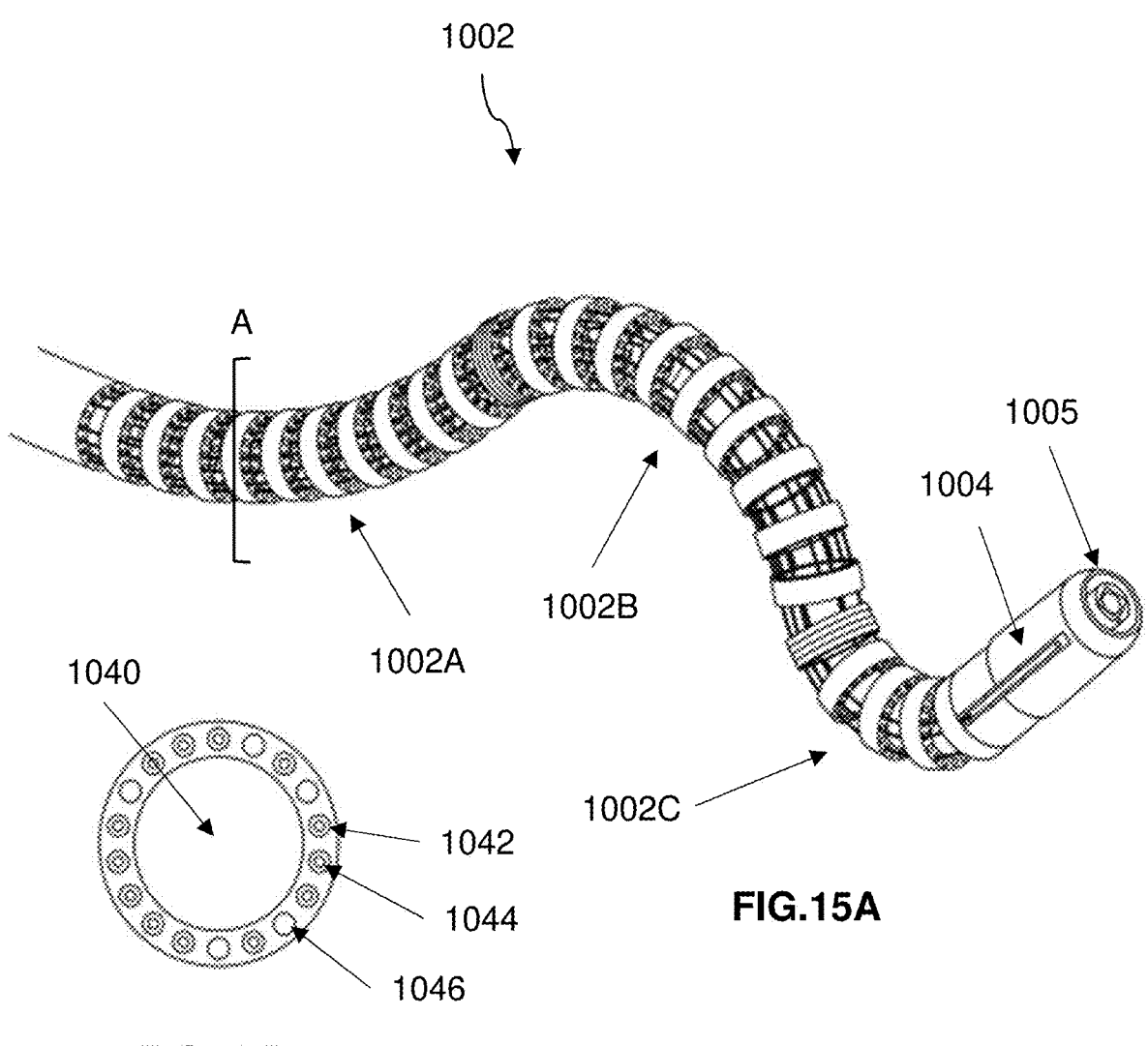
FIGS. 15A and 15B illustrate an exemplary flexible device arranged as a catheter or continuum robot configuration according to some embodiments.

FIGS. 15A and 15B show an embodiment of the continuum robot 1002. FIG. 15B is a cross-sectional view of FIG. 15A taken along line A.

In FIG. 15A, the continuum robot 1002 is configured as a catheter as the flexible device and includes a proximal section 1002A, a middle section 1002B, and a distal section 1002C. Running proximal to distal through the catheter is a hollow chamber that can be used as a working channel for medical procedures. The continuum robot 1002 includes a plurality of driving wires 1042 and supporting wires 1044 that are each located in lumen 1046 surrounding the central hollow chamber 1040, as shown in the cross-sectional view of FIG. 15B. Each section is bent by the plurality of wires (driving linear members). The posture of the continuum robot 1002 is supported by supporting wires (supporting liner members). The tracking sensor 1004 is attached to the atraumatic tip 1005 of the continuum robot 1002.

Figure 16:
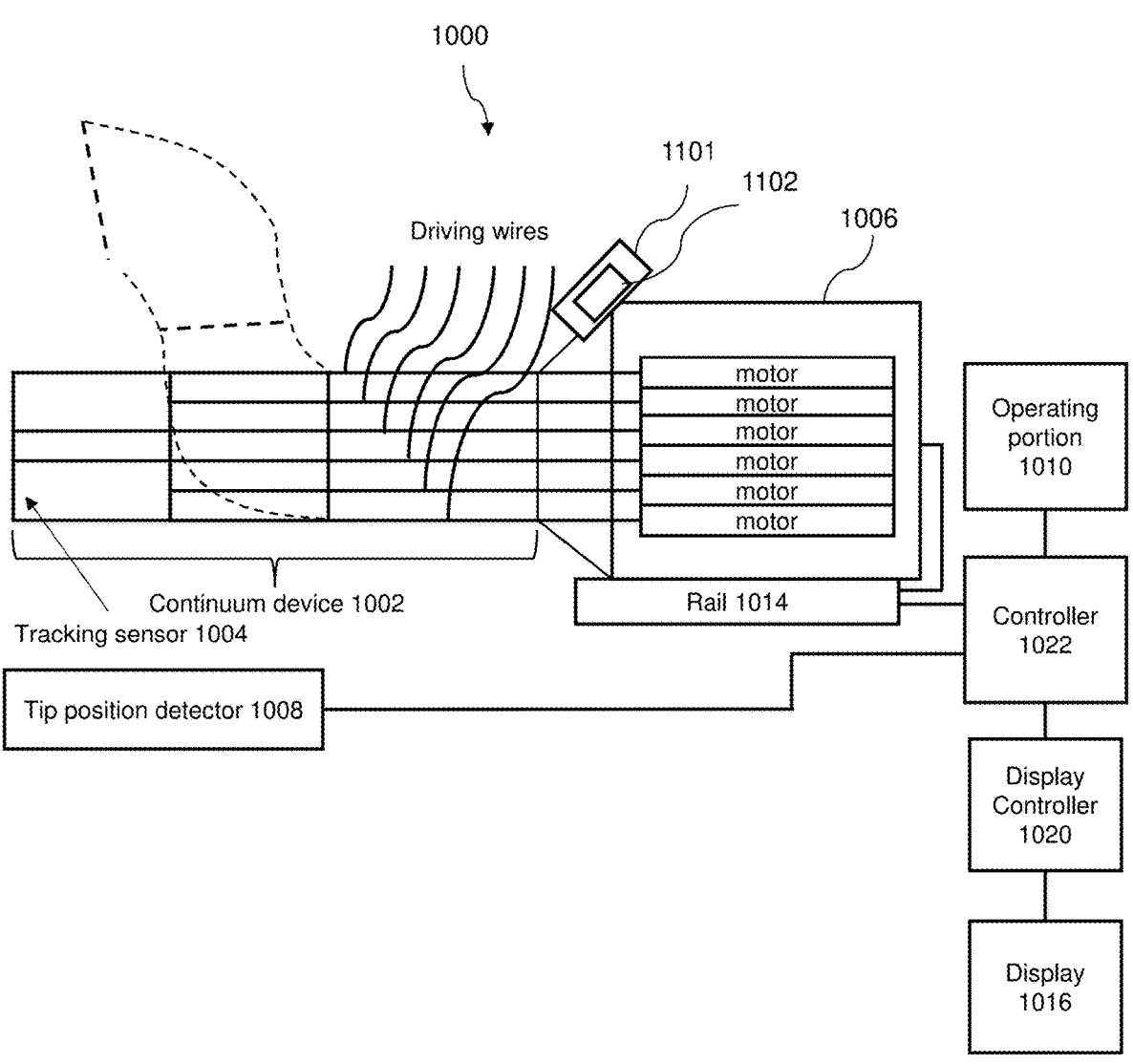
FIG. 16 is an operational diagram of the flexible device arranged as a continuum robot configuration according to some embodiments.

FIG. 16 shows an operation system of the continuum robot 1002. The driving wires are connected to actuator 1006. The actuator 1006 includes one or more motors and drives each section of the continuum robot 1002 by pushing and/or pulling the driving wires. The actuator 1006 proceeds or retreats along the rail 1014 and the actuator 1006 and continuum robot 1002 proceeds or retreats in an object or patient's body. The EM tracking sensor 1004 is attached to the tip of the continuum robot 1002.

The tip position detector 1008 detects a position of the EM tracking sensor 1004 and outputs the detected positional information to the controller 1022.

The controller 1022 receives the positional information of the tip of the continuum robot 1004 from the tip position detector 1008. The controller 1022 controls the actuator 1006 in accordance with the manipulation by a user via one or more operating portion 1010.

The controller 1022 may control the continuum robot 1002 based on an algorithm known as follow the leader (FTL) algorithm. By applying the FTL algorithm, the middle section 1002B and the proximal section 1002A (following sections) of the continuum robot 1004 move at a first position in the same way as the distal section 1002C moved at the first position or a second position near the first position.

The controller 1022 and the display controller 1020 can be configured separately. Alternatively, the controller 1022 and the display controller 1020 can be configured as one device.

The tool 1012 may be a medical tool such as an endoscope, a forceps, a needle or other biopsy tools. In this embodiment, the tool may be described as an operation tool or working tool. The working tool is inserted or removed through a working tool insertion slot 1101. An insertion/removal detector 1102 is attached to the insertion slot 1101 and detects whether the working tool is inserted into the insertion slot 1101.

Figure 17:
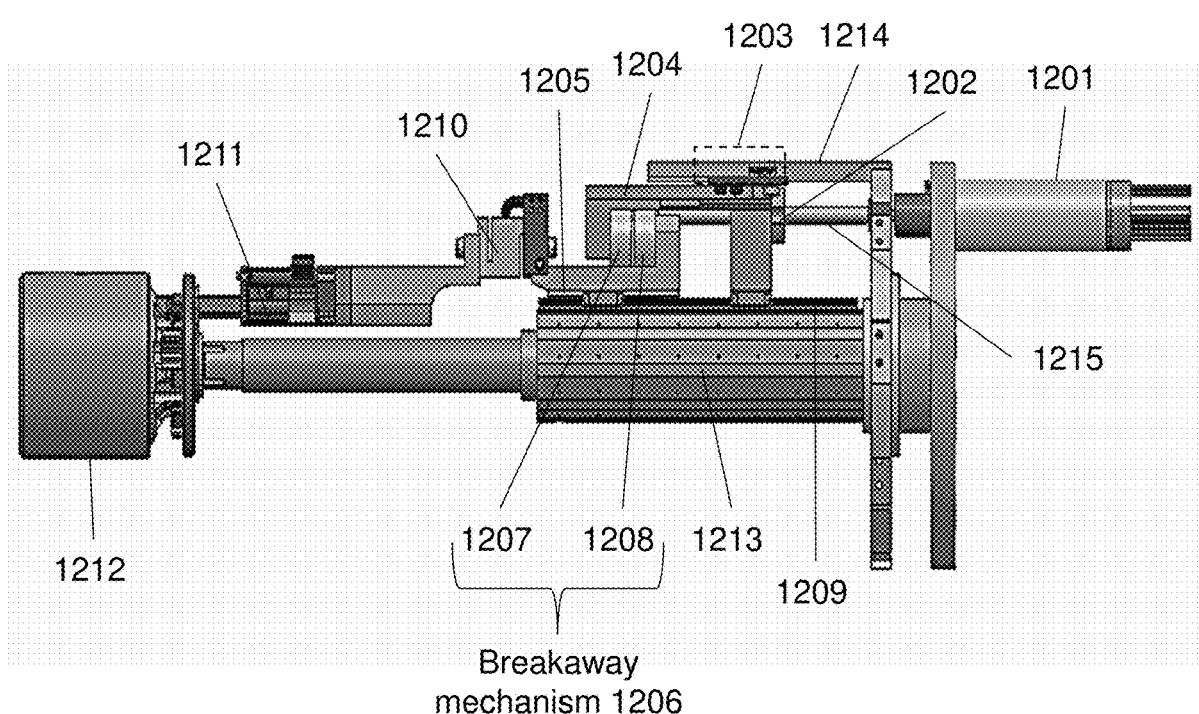
FIG. 17 illustrates an actuator mechanism according to some embodiments.

FIG. 17 shows a mechanism of the actuator 1006 according to some embodiments.

The actuator 1006 includes a motor 1201, a threaded nut 1202, a home positioning mechanism 1203, a first arm 1204, a second arm 1205, a breakaway mechanism 1206, a first member 1207, a second member 1208, a linear sliding mechanism 1209, a force sensor 1210, a wire clamping mechanism 1211, a catheter interface hub 1212, a central axis 1213, a support arm 1214, a lead screw 1215, and can include other components.

The motor 1201 is a driving unit that provides force to push and/or pull the driving wire. The lead screw 1215 and the threaded nut 1202 convert a rotational motion generated by the motor 1201 to a linear motion (push and pull motion). The threaded nut 1202 is attached to a first arm 1204 and pushes or pulls the first arm (tractor) 1204 in accordance with the driving force from the motor 1201.

The tractor is the first arm 1204 and is attachably and detachably connected to a second arm 1205 by a breakaway mechanism 1206 (breakaway connector). In this embodiment, the first arm 1204 and the second arm 1205 are magnetically connected by the breakaway mechanism 1206. A first member 1207 is fixed to the first arm 1204 and a second member 1208 is fixed to the second arm 1205. A contact surface of the first member 1207 and a contact surface of the second member 1208 are magnetically attached. In this embodiment, both of the first member 1207 and the second member 1208 are magnets. The breakaway mechanism 1206 does not necessarily have two magnets and may include more. One of the first member 1207 and the second member 1208 can be a magnet and the other member can be a metal like iron that attaches to magnets. The breakaway mechanism 1206 can be configured with a breakaway sensor that can detect when breakaway occurs. In a case where breakaway occurs and is detected by the breakaway sensor, a recovery and homing routine can be initiated, and/or an error state can be initiated that can prompt a service technician or other to diagnose the continuum robot 1004.

In this embodiment, the contact surface of the first member 1207 faces to a direction to which the first arm 1204 and/or a driving wire is pulled and the contact surface of the second member 1208 faces to a direction to which the first arm 1204 and/or the driving wire is pushed.

The first arm 1204 and the second arm 1205 are configured to slide on a linear sliding mechanism 1209. In a state where the first member 1207 and the second member 1208 are attached, the first arm 1204 and the second arm 1205 move linearly along the linear sliding mechanism 1209 if the tractor pushes or pulls the first arm 1204.

The first member 1207 and the second member 1208 are separated or detached if the first arm 1204 is pushed and a force larger than a predetermined force is applied to the first member 1207 and the second member 1208. After the first member 1207 and the second member 1208 are separated, the force transmitted by the first arm 1204 is not transmitted to the second member 1208, the second arm 1205, wire clamping mechanism 1211 and the driving wire clamped by the clamping mechanism 1211. In this way, the breakaway mechanism 1206 prevents the driving wire being pushed by a force larger than a predetermined force and prevents a tip of the continuum robot 1004 from pushing, for example, a wall of a lumen of a human's organ too much.

The wire clamping mechanism 1211 is configured to clamp an end of a driving wire of the continuum robot 1004 in a case where the continuum robot 1004 is attached to the actuator 1006 via catheter interface 1212. The clamping mechanism 1211 is pushed and/or pulled in accordance with the push and/or pull of the second arm 1205 and then the driving wire is pushed and/or pulled to a longitudional direction to bend the continuum robot 1004.

The force sensor 1210 detects a tension applied to the driving wire. The sensed signal is transmitted to the controller 1022 and the controller 1022 controls the actuator 1006 based on the sensed signal.

The home positioning mechanism 1203 is configured to return the tractor to its home position, for example, after the first member 1207 and the second member 1208 are separated or detached. The home positioning mechanism 1203 includes a sensor board and a reflective board. On a surface of the sensor board that faces to the reflective board, one or more positional sensors (e.g., photosensors, photodetectors, or the like) are mounted. The sensor board is fixed to or a part of a support arm 1214 and the reflective board is fixed to or a part of the first arm 1204.

Although, in FIG. 17, only one set of the motor 1201, the threaded nut 1202, lead screw 1215, the home positioning mechanism 1203, the first arm 1204, the second arm 1205, the first member 1207, the second member 1208, the force sensor 1210 and the wire clamping mechanism 1211 is shown for the explanation, the actuator 1006 can include each set of those features for respective wires around a central axis 1213.

Homing control sets a home position for an end of the wire. A homing control section executes the homing control when a predetermined initialization condition is satisfied. The homing control is executed by the homing control section so the breakaway mechanism returns the wire to the home position in a breakaway state. The initialization condition may have one or more condition items, and when any one of the conditions is satisfied, the initialization condition is determined to be satisfied. Accordingly, the homing control section may be configured to execute the homing control when one of the condition items is satisfied. In the homing condition, the steering signal is proportional to the rate of turn of the line of sight from sensor position to the target.

The travel limiting feature, mechanism or component can be configured as a sensor at the external tip of the flexible device, or distal end of the continuum robot or catheter. Movement of the position of the distal end of the catheter can be limited by the travel limiting feature. The travel limiting feature can be based on relative movement of the actuator and the flexible device. The guide member can be configured with a stop to limit the distal travel of the catheter tip.

Sensing element can be a sensor, transducer, or other functional element. The sensing element can produce a signal related to a parameter of the medical device or object for which a procedure is being performed. The sensing element can produce a signal related to a variety of parameters including the position, temperature, pressure, movement, travel distance, or other parameter.

The home positioning mechanism is explained with reference back to FIGS. 8 and 9.

As explained above, the home positioning mechanism 1203 includes a sensor board and a reflective board.

The reflective board is compatible with the photosensors (a home positioning sensor and a limitation sensor) is attached to the first arm 1204 that is connected with the motor 1201, not with a second arm 1205 that is connected with the wire. The photosensors output a high signal when the photosensors detects a reflection from the reflective board and output a low signal when the photosensors do not detect the reflection from the reflective board.

The home positioning sensor and the traveling limitation sensor are arranged at a different position from each other along a direction perpendicular to the longitudional direction and the length of the first reflective board is shorter than the length of the second reflective board. In this embodiment, the home positioning sensor and the traveling limitation sensor are arranged diagonal on the sensor board.

The reflective board is fixed to or a part of the first arm 1204 and the reflective board travels along with the first arm 1204. The sensor board on which the photosensor exists is fixed to the support arm 1214. The first arm 1204 is configured to slide along the linear sliding mechanism. The first arm 1204 has a reflective board of which reflective surface faces to a direction that the photosensor exists. The reflective board is configured so that in a case where the first arm 1204 is at a motor side of the home position, the first channel of the reflective board faces to the photosensor and the reflection from the first channel of the reflective board is detected by the homing sensor.

In addition, the reflective board is configured so that in a case where the first arm 1204 is at the other side (continuum robot 1002 side and/or wire clamping mechanism 1211 side) of the home position, the first channel of the reflective board does not face to the photosensor and the reflection from the reflective board is not detected by the photosensor.

The homing channel has a first channel and a second channel, and can include other channels. The first channel contains a reflective surface for only one half of travel, where the sensor will be triggered 'ON' for the first half of travel and 'OFF' the second half. When the homing routine is engaged an on signal (State A) will tell the actuator to move the tractor in toward the positive direction (for example, to the direction the first arm 1204 is pushed) until the state is triggered off. This will indicate that the tractor has reached the home position. Similarly, if the homing routine is enabled with an 'OFF' signal (State B), the tractor will move in the opposite direction (for example, to the direction the first arm is pulled) to find home. Additionally, in state B, the tractor can move a small distance past the home position and return the other way until the sensor is triggered again. This will account for hysteresis error in the sensor 110 and allow for better homing accuracy, e.g., unidirectional homing.

The home position can vary and does not necessarily be the center or a half of the travel. The home position can be located anywhere in the travel of the first arm 1204 and the length of the first channel of the reflective board can be determined in accordance with the position of the home position.

The second channel can be configured as a limit channel. The limit channel is used for detecting the end of travel to prevent tractor collision and jamming. In the limit channel, the reflective surface in the center drops off on both edges of travel before the end of travel hard stop is hit. With a combination of both limit and home channels, the apparatus can now detect both the limit position of travel and which limit is positive or negative. Without the homing channel, the apparatus 100 would know if it reached a limit, but would not know which limit and therefore would not know with direction to move.

Figure 18:
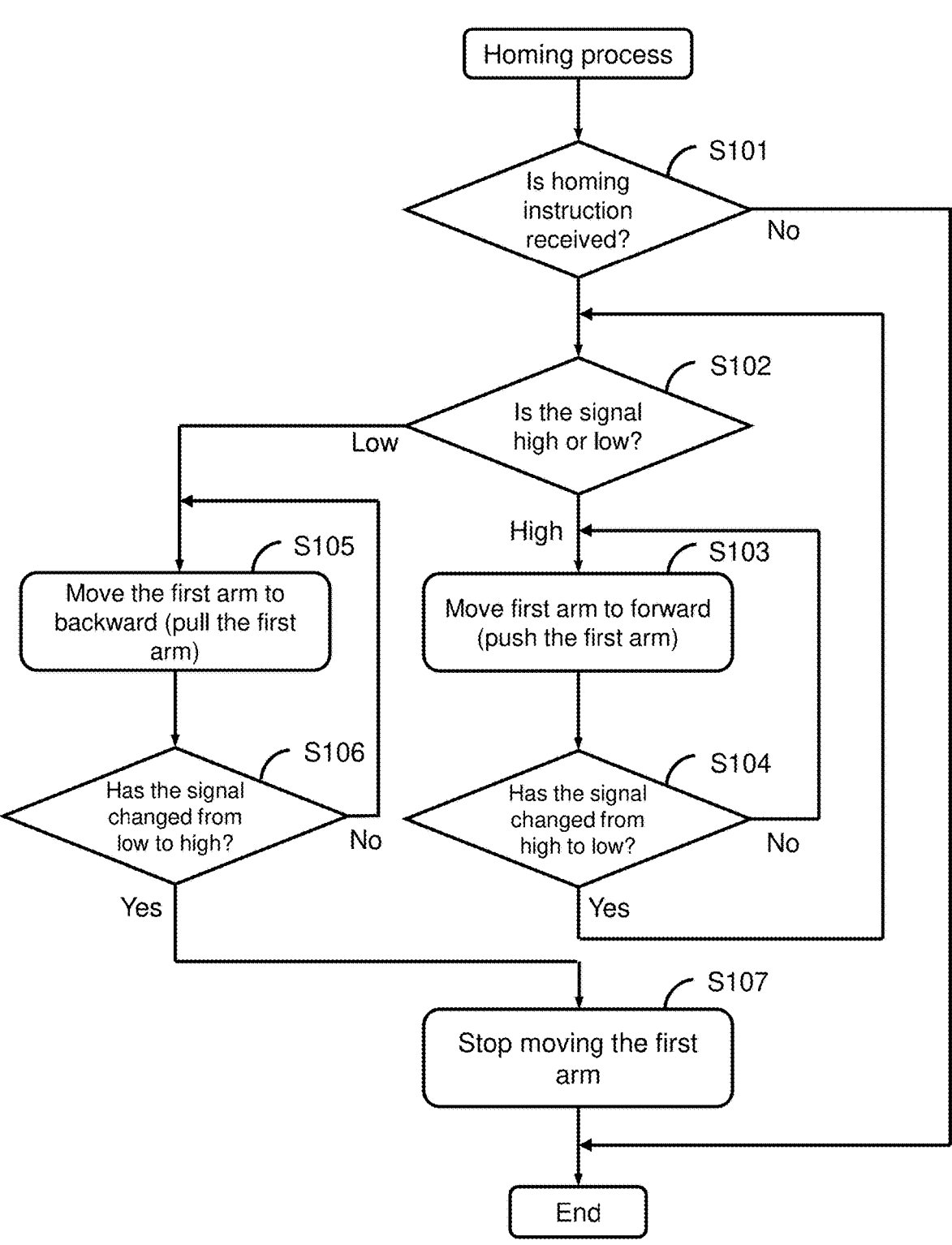
FIGS. 18 and 19 are flow charts of a homing process according to some embodiments.

FIG. 18 is a flowchart of a homing process according to some embodiments. The homing process is performed by one or more processors of the controller 1022 by executing instructions stored in one or more memory of the controller 1022.

In step S101, the processor determines whether a homing instruction is received. For example, the homing instruction is received in accordance with an instruction by a user. Alternatively, the homing instruction may be received automatically in accordance with an occurrence of a certain event. The event may be a detection of the disconnection of the first arm 1204 and the second arm 1205. The processor is configured to detect the disconnection based on the signal from the force sensor 1210 and the driving status of the motor 1201. In a case where the first arm 1204 and the second arm 1205 are disconnected, even if the motor 1201 drives first arm 1204, the second arm 1205 does not move. Then the force sensor 1210 does not detect a change of tension of the driving wire while the motor 1201 is driving. In such status, the controller 1022 can determine that the first arm 1204 and the second arm 1205 are disconnected.

In a case where the homing instruction is not received ("No" in step S101), the homing process is not performed. In a case where the homing instruction is received, the controller 1022 determines whether the signal from the homing sensor is high (first state) or low (second state) (step S102). In this embodiment, in a case where the first channel of the reflective board faces to the photosensor and the reflection from the first channel of the reflective board is detected by the homing sensor, the homing sensor outputs high signal. In addition, in a case where the first channel of the reflective board does not face to the homing sensor and the reflection from the reflective board is not detected by the homing sensor, the homing sensor outputs a low signal. In a case where the signal is high, the process proceeds to step S103. In a case where the signal is low, the process proceeds to step S105.

The determination in S101 is not limited to determining whether the signal is high or low. The controller 1022 may determine whether the signal is higher than a predetermined threshold or not. In a case where the signal is higher than the threshold, the process proceeds to step S103 and in a case where the signal is lower than the threshold, the process proceeds to step S105. Multiple thresholds may be used. For example, in a case where the signal is higher than a first threshold, the process proceeds to step S103 and in a case where the signal is lower than a second threshold which is lower than the first threshold, the process proceeds to S105.

In step S103, the controller 1022 controls the motor 1201 to push and move forward the first arm 1204.

In step S104, the controller 1022 determines whether the signal is changed from high to low. If the signal is changed to low, the controller 1022 returns back to the step S102. If the signal has not changed to low, the controller 1022 returns back to step S103.

Figure 19:
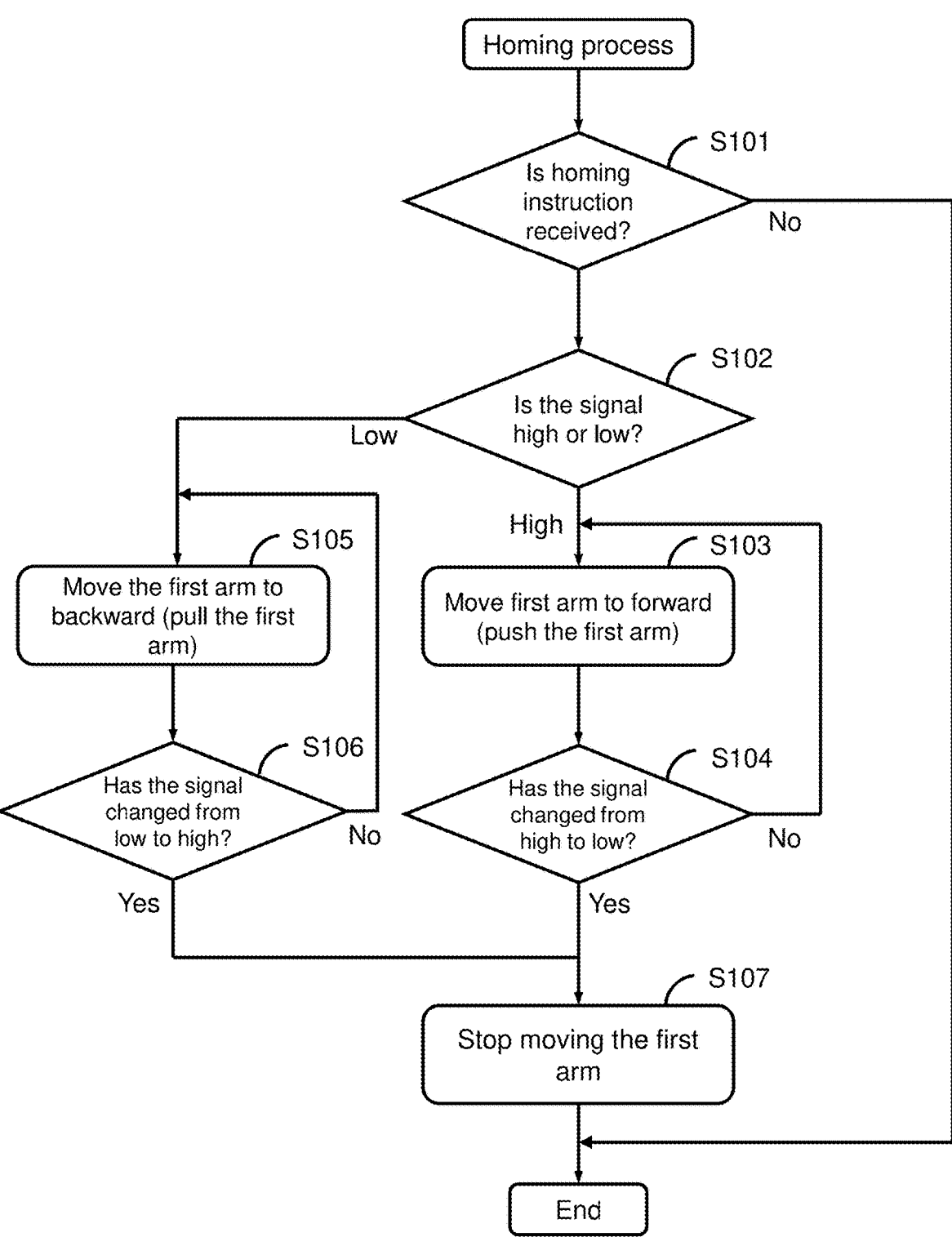

In an alternative embodiment, as shown in FIG. 19, if the signal is changed to low ("Yes" in step S104), the controller can control the motor 1201 to stop the first arm in step S107. In that case, a position where the signal is changed from high to low and a position where the signal is changed from low to high are defined as the home position. However, in that case, those positions may not be the same positions because of a momentum of the first arm and consequently, the home position may vary depending on whether the signal is changed from low to high or high to low. To let the first arm stop at the same position consistently, in the embodiment shown FIG. 18, the first arm keeps moving even if the signal is changed from high to low ("Yes" in step S104) with the signal being low and moves to step S105 via step S102 to change the moving direction of the first arm from forward to backward. As described below, if the signal is changed to high ("Yes in step S106"), the controller 1022 controls the motor 1101 to stop the first arm in step S107. In this way, the first arm can be stopped at the same position because the control of the moving of the first arm is performed while the first arm is moving to the same direction (in this embodiment, the direction is backward).

A moving speed of the first arm while the signal is high can be faster than a moving speed of the first arm after the signal is changed from high to low and the moving direction of the first arm is changed to backward. In this way, the first arm can be moved to around the home position speedily with a fast moving speed while the first arm can be stopped at the home position finely with a slow moving speed.

In step S105, the controller 1022 controls the motor 1101 to pull and move backward the first arm 104.

In step S106, the controller 1022 determines whether the signal is changed from low to high. If the signal is changed to high, the controller 1022 controls the motor 1101 to stop the first arm in step S107. If the signal has not changed to low, the controller 1022 returns back to step S105.

Again, the signal high can be a signal higher than the first threshold and the signal low can be a signal lower than the second threshold which is lower than the second threshold. Alternatively, the first threshold and the second threshold can be the same value.

The homing process is not limited to the process shown in FIG. 13. For example, in step S104, the controller can proceed to the process of step S107 if the signal is changed to low ("Yes" in step S104), while the controller returns to S102 if the signal is changed to high in step S106 ("Yes" in step S106).

While with just a homing sensor, the limits can be inferred through software, there is still a safety concern of reaching the end of travel. Therefore a second channel in the form of a limit channel is provided for detecting the end of travel to prevent tractor collision and jamming. The limit channel includes a reflective surface generally in the center that falls off on both edges of travel before the end of travel hard stop is hit. With the combination of both a limit channel and a home channel, the apparatus 1000 can now detect both the limit positon of travel and which limit is positive or negative. Without the homing channel the apparatus 1000 would know it reached a limit, but would not know which limit and therefore would not know which direction to move.

Figure 20:
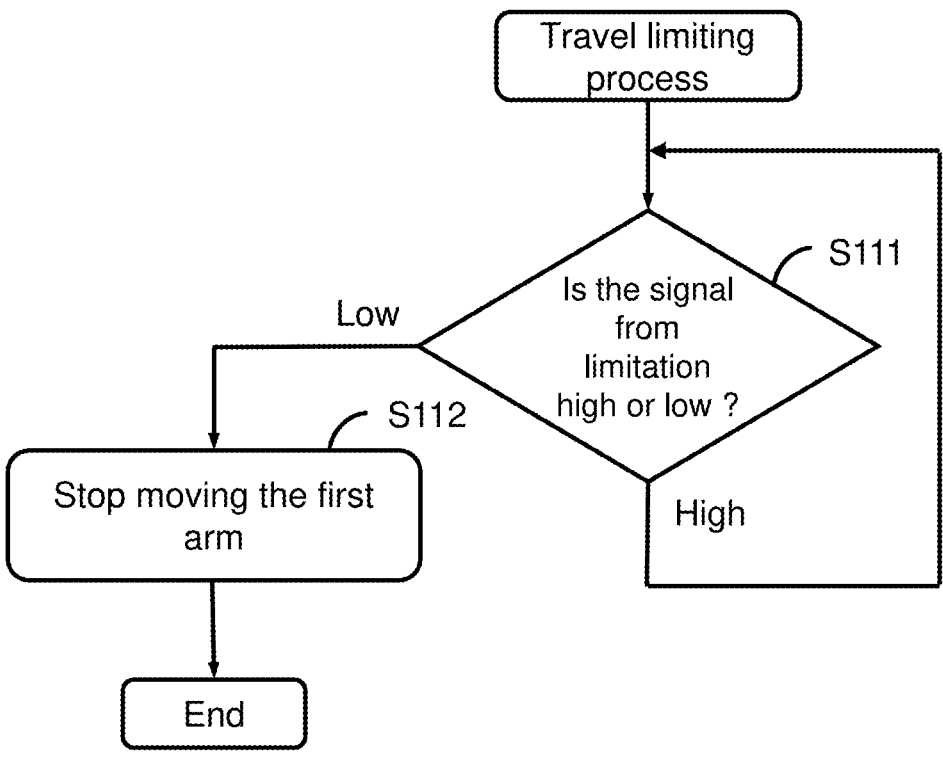
FIG. 20 is a flow chart of a travel limiting process according to some embodiments.

FIG. 20 is a flowchart of a travel limiting process. This travel limiting process is performed by one or more processors of the controller 1022 by executing instructions stored in one or more memory of the controller 1022.

The controller 1022 determines whether the signal from the limitation sensor is high (third state) or low (fourth state) (step S111). In this embodiment, in a case where the second channel of the reflective board faces to the limitation sensor and the reflection from the second channel of the reflective board is detected by the limitation sensor, the limitation sensor outputs high signal. In addition, in a case where the second channel of the reflective board does not face to the limitation sensor and the reflection from the second channel of the reflective board is not detected by the limitation sensor, the limitation sensor outputs low signal. In a case where the signal is high, the process repeats step S1201. In a case where the signal is low, the process proceeds to step S112.

In step S112, the controller 1022 controls the motor 1201 to stop the first arm 1204 from moving and the process ends.

In this embodiment, the length of the second channel of the reflective board corresponds to length within which the first arm 1204 can travel.

Figure 21:
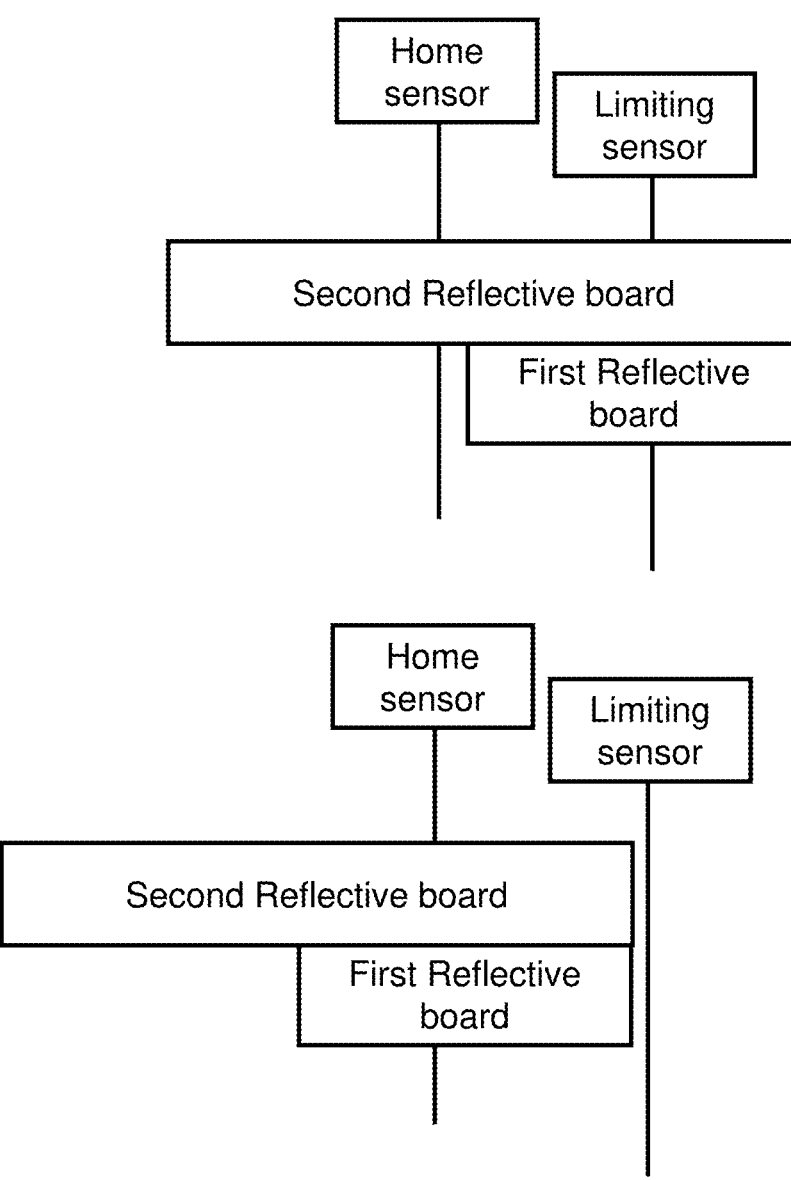
FIG. 21 is an operational diagram of the home sensor and the limiting sensor with reflective boards according to some embodiments.

FIG. 21 shows an operational diagram the home sensor and the limiting sensor with a plurality of reflective boards according to some embodiments, where the length of the first channel of the reflective board (for homing) can be shorter than the length of the second channel (for limiting) of the reflective board. In this embodiment, the first channel and the second channel of the reflective board can be configured as one board. The lengths of the first and second channels, as well as any other channels can vary according to a desired configuration, the length of the first channel can be less than, equal to, or greater than the length of the second channel.

Figure 22:
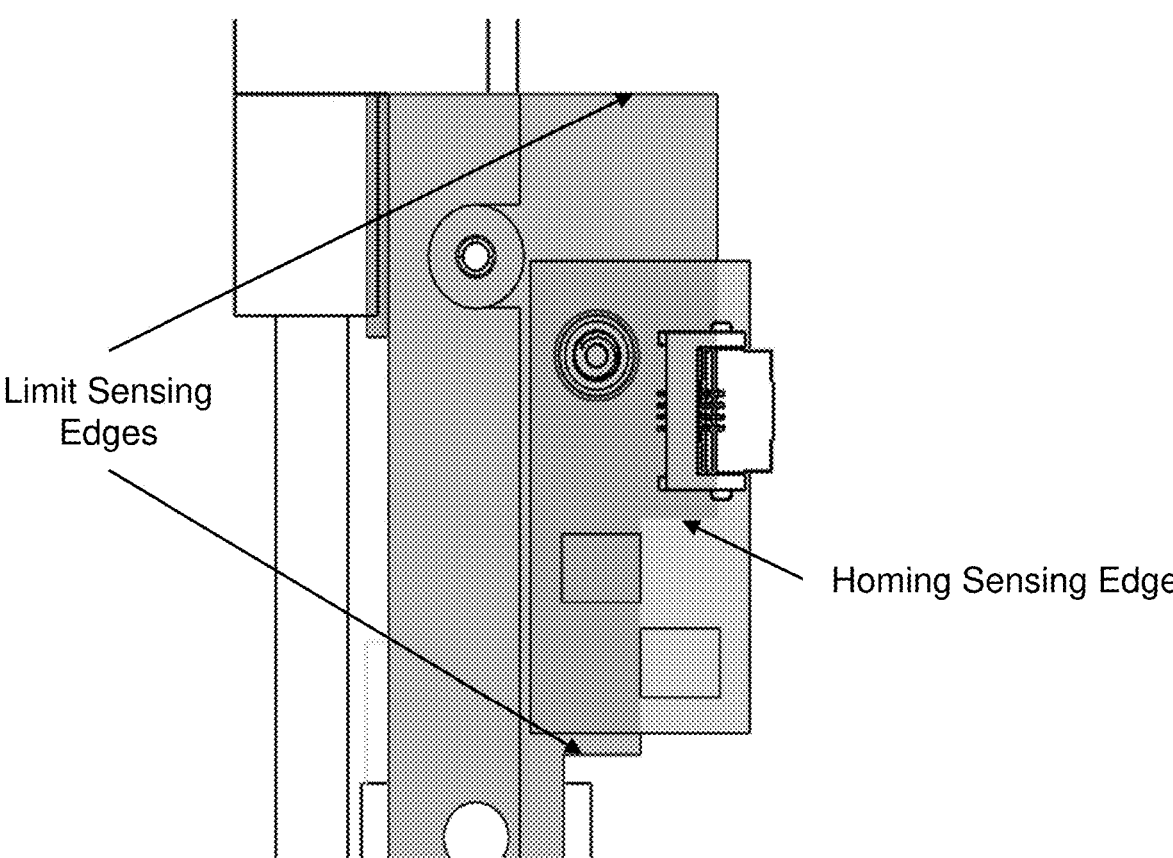
FIGS. 22 and 23 illustrate the homing sensing edge and limit sensing edges according to some embodiments.
Figure 23:
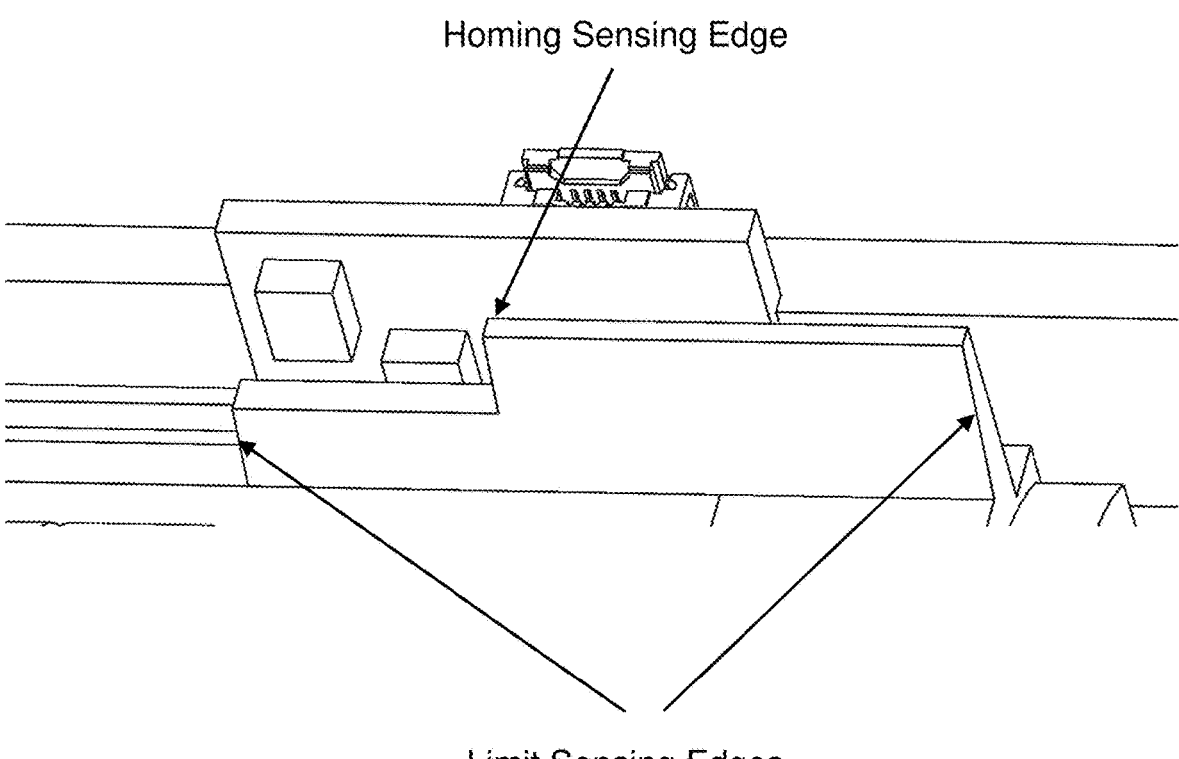

FIGS. 22 and 23 illustrate the homing sensing edge and limit sensing edges according to some embodiments. The homing sensing edge and the limit sensing edges can be located on the reflecting board.

Figure 24:
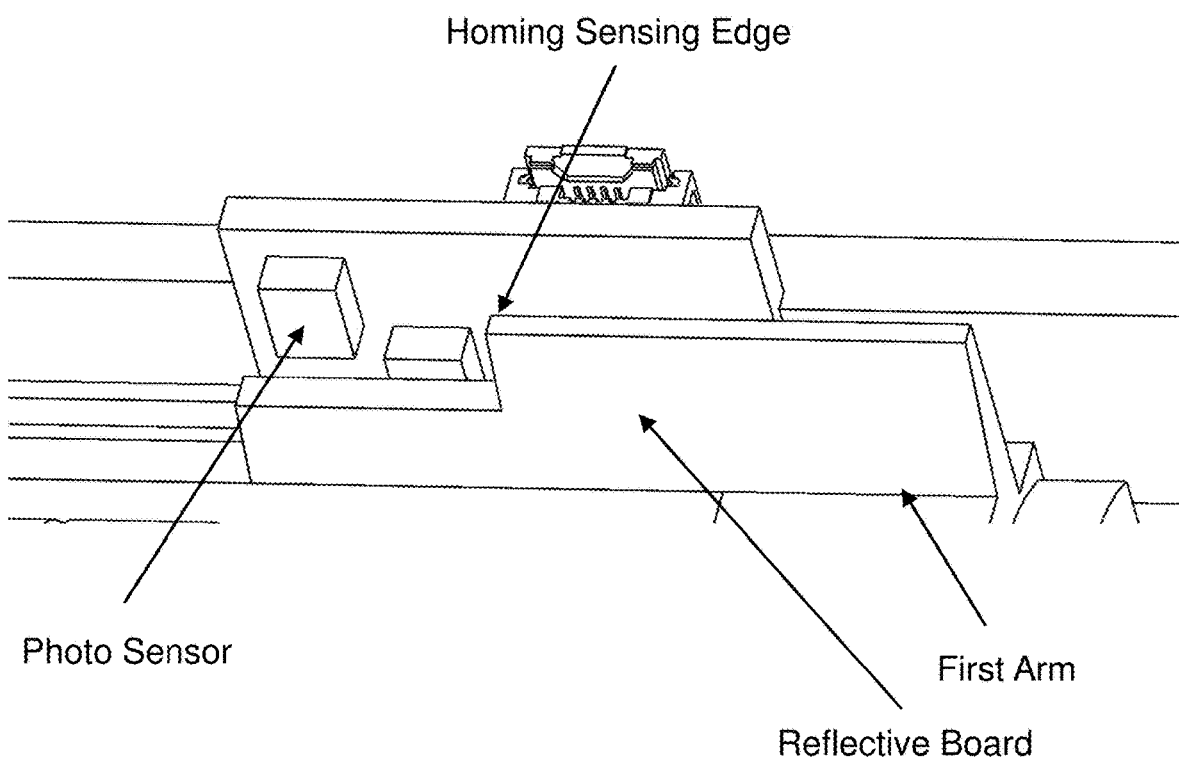
FIG. 24 illustrates the homing sensing edge with a reflector board and a photo sensor according to some embodiments.

FIG. 24 illustrates the homing sensing edge and limit sensing edges according to some embodiments. The reflective board is mounted on the first arm and the homing sensing edge can be located on the reflecting board. A photo sensor can be mounted on the blocking board. There are two separate reflective boards having different lengths in FIG. 24. Other configurations are possible.

Figure 25:
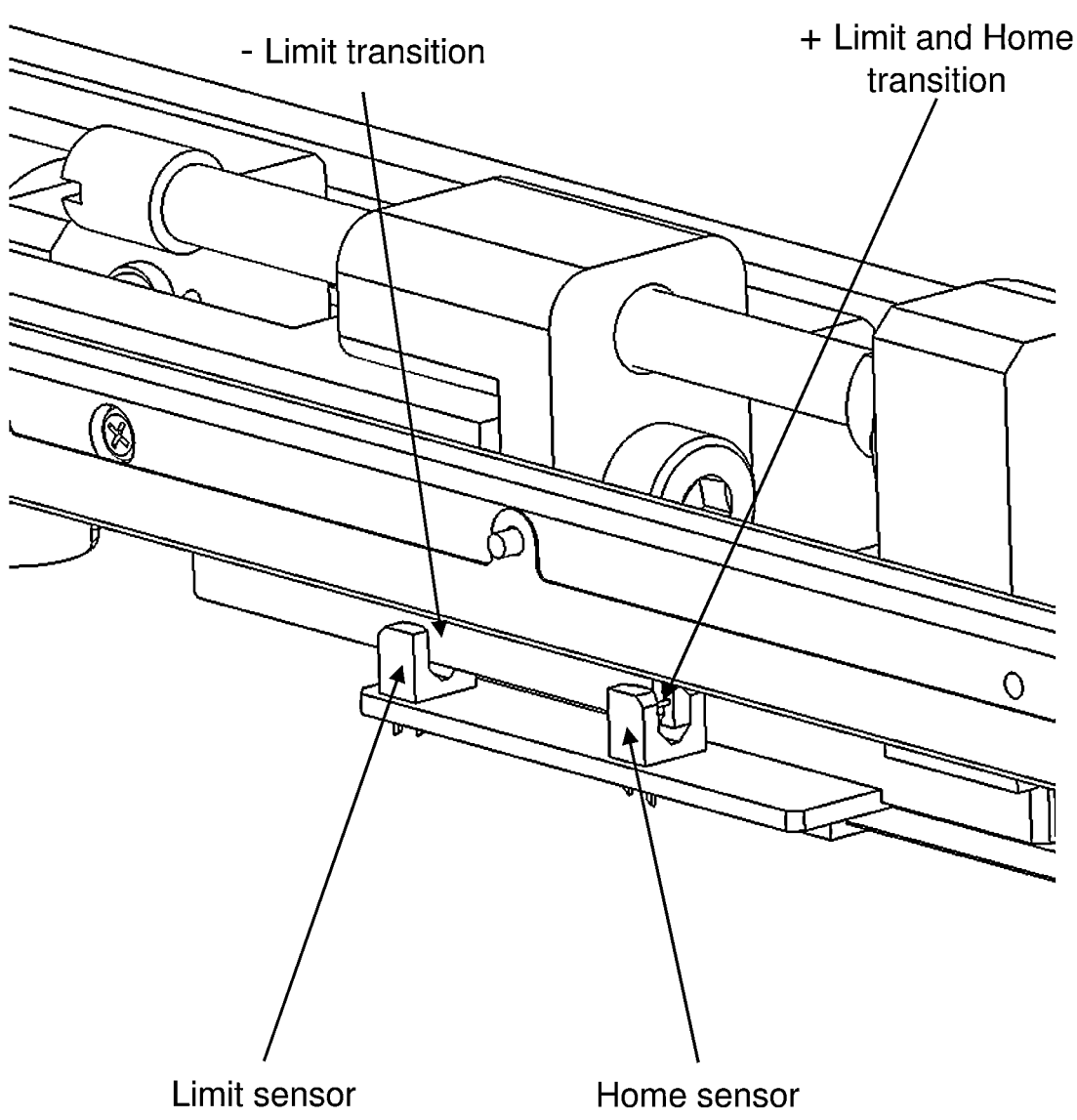
FIG. 25 illustrates an operational diagram of the limit transition and limit and home transition according to some embodiments.

FIG. 25 illustrates the home sensor and limit sensor configured to be mounted on a blocking board for both the negative limit transition and the positive limit and home transition. A reflective board can work in this configuration. The blocking board can be the same for both the limit sensor and the home sensor and, thus, have the same length. This can be advantageous because there are less parts and less cost. However, the sensors should be precisely placed at a distance equal to half the board length so the limit is in the center when home is at the edge. In an alternative embodiment, separate boards can be used for each channel which allows the sensors to be placed closer together. Then they would not need to be spatially constrained to each and could be placed at appropriate places on the boards.

FIG. 26 is a flow chart of a method of moving a wire with a reflective board according to some embodiments.

Step S121 includes moving the wire an actuator along a longitudinal direction. Step S122 includes connecting a tractor to the wire to move the wire along the longitudinal direction. Step S123 includes providing a reflective board with a first channel and a second channel. Step S124 includes detecting reflection light from the reflective board with a first sensor to determine a home position. Step S125 includes determining a home position with a first sensor. Step S126 includes determining a limit position of travel with a second sensor. Step S127 includes arranging the first sensor and the second sensor at a different position from each other along a direction perpendicular to the longitudinal direction.

Figure 27:
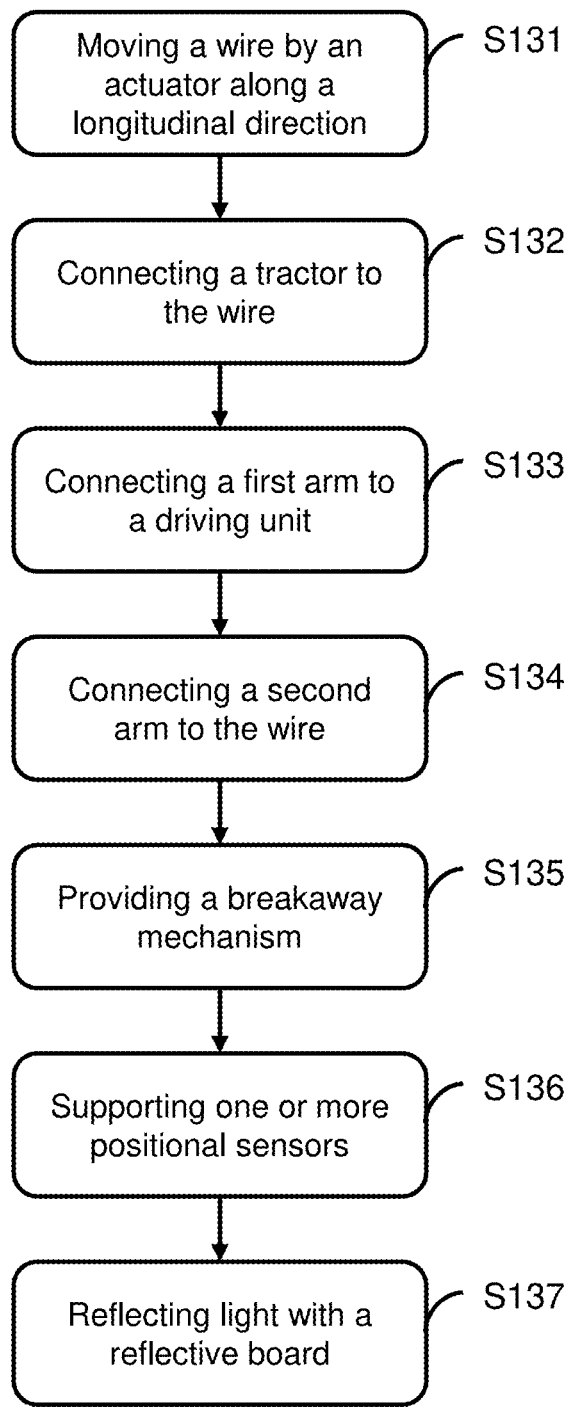
FIG. 27 is a flow chart of a method of moving a wire with a reflective board according to some embodiments.

FIG. 27 is a flow chart of a method of moving a wire with a reflective board according to some embodiments.

Step S131 includes moving a wire by an actuator along a longitudinal direction. Step S132 includes connecting a tractor to the wire to move the wire along the longitudinal direction. Step S133 includes connecting a first arm to a driving unit that drives the first arm to the longitudinal direction. Step S134 includes connecting a second arm to the wire. Step S135 includes providing a breakaway mechanism that can include a breakaway connector configured to connect and disconnect the first arm and the second arm. Step S136 includes supporting at least one positional sensor by a support member. Step S137 includes reflecting light with a reflective board so that the at least one positional sensor can detect the light reflected by the reflective board, wherein the first arm includes the reflective board.

Figure 28:
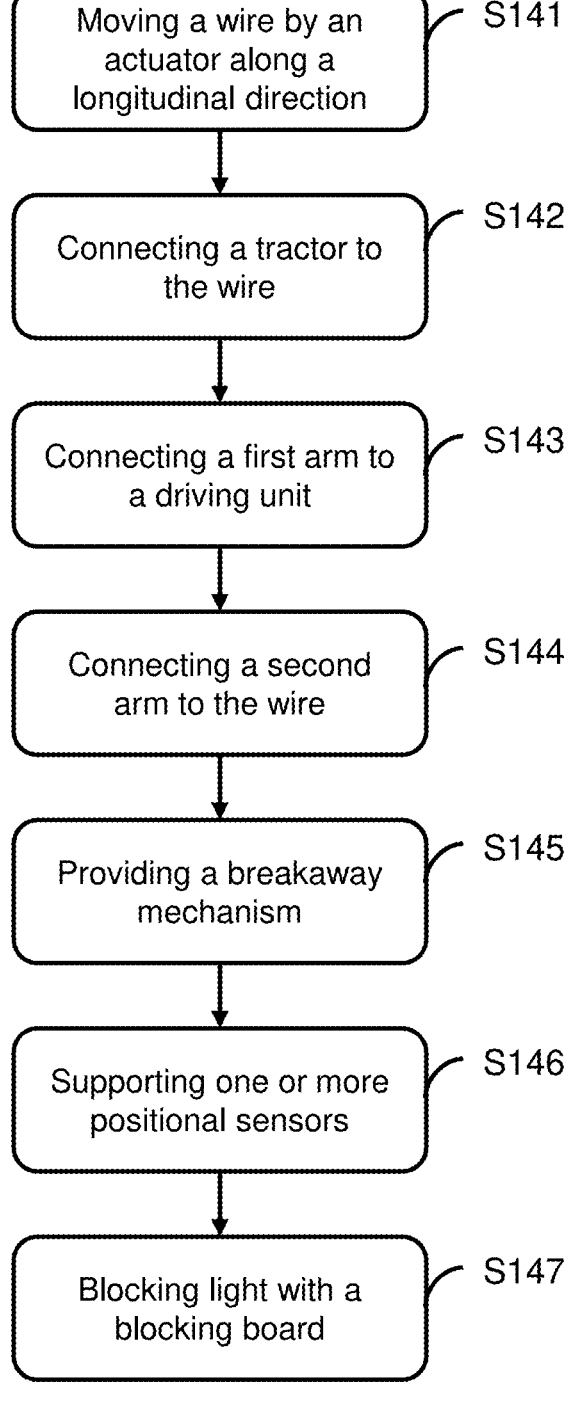
FIG. 28 is a flow chart of a method of moving a wire with a blocking board according to some embodiments.

FIG. 28 is a flow chart of a method of moving a wire with a blocking board according to some embodiments.

Step S131 includes moving a wire by an actuator along a longitudinal direction. Step S132 includes connecting a tractor to the wire to move the wire along the longitudinal direction. Step S133 includes connecting a first arm to a driving unit that drives the first arm to the longitudinal direction. Step S134 includes connecting a second arm to the wire. Step S135 includes providing a breakaway mechanism that can include a breakaway connector configured to connect and disconnect the first arm and the second arm. Step S136 includes supporting at least one positional sensor by a support member. Step S137 includes reflecting light with a reflective board so that the at least one positional sensor can detect the light reflected by the reflective board, wherein the first arm includes the reflective board.

Preferably, according to some embodiments, the implementation combines the home reflective board, limit reflective board, and tractor into a single component. This is beneficial to reduce cost and tolerance stack up. Also, both sensors can be mounted to a single printed circuit board assembly (PCBA) allowing for reduction in parts and cables.

Preferably, according to some embodiments, the limit sensor and homing sensor can be discrete components, as in separate PCBAs and reflective boards. This may be beneficial for scenarios with special space constraints. Also, this may reduce the chance of noise and crosstalk between channels. An additional benefit to having a separate part for the limit board is the limit position can be adjusted to shorten travel to a desired stroke, which is beneficial for prototyping purposes.

The reflective board can be fixed to the support arm 1214 and the sensor board can be fixed to the first arm 1204.

The reflective board can be configured so that in a case where the first arm 1204 is at a motor side of the home position, the first channel of the reflective board does not face to the photosensor (a home positioning sensor or a limitation sensor) and the reflection from the first channel of the reflective board is not detected by the homing sensor.

In addition, the reflective board is configured so that in a case where the first arm 1204 is at the other side (continuum robot 104 side and/or wire clamping mechanism 1211 side) of the home position, the first channel of the reflective board faces to the photosensor and the reflection from the first channel of the reflective board is detected by the photosensor.

In this case, the controller controls the motor to push and move forward the first arm 1204, in a case where the signal from the photosensor is low. In addition, the controller controls the motor 1201 to pull and move backward the first arm 1204, in a case where the signal from the photosensor is high.

Advantages

The integration of home and limit sensors together prevents the chance of a tractor experience in a crash situation where the tractor gets jammed requiring maintenance.

Key Features

An actuator that moves the wire along a longitudinal direction.

A tractor that is connected to the wire and moves the wire along a longitudinal direction.

A home positioning sensor.

A traveling limitation sensor, wherein the home positioning sensor and the traveling limitation sensor are arranged at a different position from each other along a direction perpendicular to the longitudinal direction.

A first channel of a blocking board or reflective board for the home positioning sensor.

A second channel of the blocking board or reflective board for the traveling limitation sensor, wherein the length of the first channel of the blocking board or reflective board is shorter than the length of the second channel of the reflective board, wherein the first channel of the reflective board and the second channel of the reflective board move along with a movement of the tractor.

The actuator can further include a controller, wherein in a case where a detection state of the home position sensor changes from a first state where a reflection from the first reflective board is detected to a second state where the reflection from the first reflective board is not detected, the controller determines the tractor is at a home position, and wherein in a case where a detection state of the traveling limitation sensor changes from a third state where a reflection from the second reflective board is detected to a fourth state where the reflection from the second reflective board is not detected, the controller determines the tractor is at a limit position.

The actuator can further arrange the home positioning sensor and the traveling limitation sensor at a different position from each other along a longitudinal direction.

Snake Robot

The present disclosure can be configured to be a feature of a steerable device, for example, a snake robotic catheter or the like.

As described above, the present disclosure advantageously provides solutions to re-engage breakaway and to integrate homing control and travel limiting control together to prevent the chance of a tractor experience of a crash situation where the tractor gets jammed.

According to some embodiments, an apparatus can include an actuator configured to move a wire along a longitudinal direction, a tractor that is connected to the wire and is configured to move the wire along the longitudinal direction, a driving unit, a first arm connected to the driving unit that drives the first arm to the longitudinal direction, a board connected to the first arm, a second arm connected to the wire, a plurality of sensors that can include at least a first sensor and a second sensor arranged at a different position from each other along a direction perpendicular to the longitudinal direction, at least one positional sensor configured to detect light from the board, a support member configured to support at least one positional sensor, and a breakaway mechanism that can include a breakaway connector configured to connect and disconnect the first arm and the second arm.

The breakaway mechanism can be configured to disconnect the actuator and the tractor in a case where an applied force is greater than a predetermined value. The breakaway mechanism can include a breakaway sensor configured to detect when breakaway occurs. In a case where breakaway detected by the breakaway sensor, a recovery and homing routine can be initiated, and/or an error state can be initiated that can prompt a service technician or other to diagnose the apparatus. The breakaway mechanism can be configured to return the tractor to home position in a case where breakaway occurs. The second arm can be moved to the longitudinal direction while the first arm and the second arm is connected by the breakaway connector and the first arm is driven by the driving unit.

The board can include a first channel and a second channel. The first channel and the second channel of the board can each have a length, wherein the length of the first channel is shorter than the length of the second channel. The first channel and the second channel of the board can be configured to move along with movement of the tractor.

The at least one positioning sensor can include at least a first sensor and a second sensor that are arranged at a different position from each other along a direction perpendicular to the longitudinal direction. The wire can include a plurality of wires. The apparatus can include one or more force sensors configured to measure push and pull forces on the wire, one or more wire clamping mechanisms, one or more linear sliding mechanisms, and can include other components.

The apparatus can further include a driving unit, wherein the first arm is connected to the driving unit that drives the first arm to the longitudinal direction, wherein the breakaway mechanism can include a breakaway connector configured to connect and disconnect the first arm and the second arm, and wherein the second arm is moved to the longitudinal direction while the first arm and the second arm is connected by the breakaway connector and the first arm is driven by the driving unit.

The board can be a blocking board. The at least one positioning sensor can include a sensor configured to detect light that is blocked by the blocking board and determine a home position. The at least one positioning sensor can include a sensor configured to detect light that is blocked by the blocking board and determine a limit position of travel. The blocking board can be configured to provide a negative limit transition and a positive limit and home transition. The blocking board can include a first blocking board and a second blocking board.

The apparatus can further include a controller, wherein in a case where a detection state of the at least one positioning sensor changes from a first state where a blocking of light by the first blocking board is detected to a second state where the blocking of the light by the first blocking board is not detected, the controller determines the tractor is at a home position, and wherein in a case where a detection state of the at least one positioning sensor changes from a third state where a blocking of light by the second blocking board is detected to a fourth state where the blocking of light by the second blocking board is not detected, the controller determines the tractor is at a limit position.

The apparatus can further include a first arm, and a second arm, and a driving unit, wherein the first arm is connected to the driving unit that drives the first arm to the longitudinal direction, wherein the second arm is connected to the wire, and wherein the breakaway mechanism can include a breakaway connector configured to connect and disconnect the first arm and the second arm, wherein the second arm is moved to the longitudinal direction while the first arm and the second arm is connected by the breakaway connector and the first arm is driven by the driving unit.

According to some embodiments, a method can include moving a wire by an actuator along a longitudinal direction, connecting a tractor to the wire to move the wire along the longitudinal direction, connecting a first arm to a driving unit that drives the first arm to the longitudinal direction, connecting the first arm to a board, connecting a second arm to the wire, providing at least one positional sensor configured to detect light from the board, supporting the at least one positional sensor on a support member, and providing a breakaway mechanism that can include a breakaway connector configured to connect and disconnect the first arm and the second arm.

According to some embodiments, a non-transitory storage medium storing a program can cause a computer to execute a method including moving a wire by an actuator along a longitudinal direction, connecting a tractor to the wire to move the wire along the longitudinal direction, connecting a first arm to a driving unit that drives the first arm to the longitudinal direction, connecting the first arm to a board, connecting a second arm to the wire, providing at least one positional sensor configured to detect light from the board, supporting the at least one positional sensor on a support member; and providing a breakaway mechanism that can include breakaway connector configured to connect and disconnect the first arm and the second arm.

According to some embodiments, an apparatus can include an actuator configured to move a wire along a longitudinal direction, a tractor that is connected to the wire and is configured to move the wire along the longitudinal direction, a board that can include at least a first channel and a second channel, and a plurality of sensors that can include at least a first sensor and a second sensor arranged at a different position from each other along a direction perpendicular to the longitudinal direction, wherein the first sensor is configured to determine a home position, and wherein the second sensor configured to determine a limit position of travel based on emitted light.

The first channel and the second channel of the board each have a length, wherein the length of the first channel is shorter than the length of the second channel. The first channel and the second channel of the board can be configured to move along with movement of the tractor.

The board can be a blocking board. The first sensor can include a home positioning sensor configured to detect light that is blocked by the blocking board and determine a home position. The second sensor can include a traveling limitation sensor configured to detect light that is blocked by the blocking board and determine a limit position of travel. The blocking board can be configured to provide a negative limit transition and a positive limit and home transition. The blocking board can include a first blocking board and a second blocking board.

The apparatus can further include a controller, wherein in a case where a detection state of the first sensor changes from a first state where a blocking of light by the first blocking board is detected to a second state where the blocking of the light by the first blocking board is not detected, the controller determines the tractor is at a home position, and wherein in a case where a detection state of the second sensor changes from a third state where a blocking of light by the second blocking board is detected to a fourth state where the blocking of light by the second blocking board is not detected, the controller determines the tractor is at a limit position.

The board can be a reflective board. The first sensor can include a home positioning sensor and the first sensor can include a home positioning sensor configured to detect reflection light from the reflective board and determine a home position. The second sensor can include a traveling limitation sensor configured to detect reflection light from the reflective board and determine a limit position of travel. The reflective board can be configured to provide a negative limit transition and a positive limit and home transition. The reflective board can include a first reflective board and a second reflective board.

The apparatus can further include a controller, wherein in a case where a detection state of the first sensor changes from a first state where a reflection from the first reflective board is detected to a second state where the reflection from the first reflective board is not detected, the controller determines the tractor is at a home position, and wherein in a case where a detection state of the second sensor changes from a third state where a reflection from the second reflective board is detected to a fourth state where the reflection from the second reflective board is not detected, the controller determines the tractor is at a limit position.

The wire can include a plurality of wires. The apparatus can include one or more force sensors configured to measure push and pull forces on the wire, one or more wire clamping mechanisms, one or more linear sliding mechanisms, and can include other components.

The apparatus can include a breakaway mechanism configured to disconnect the actuator and the tractor in a case where an applied force is greater than a predetermined value. The breakaway mechanism can include a breakaway sensor configured to detect when breakaway occurs. In a case where breakaway detected by the breakaway sensor, a recovery and homing routine can be initiated, and/or an error state can be initiated that can prompt a service technician or other to diagnose the apparatus. The breakaway mechanism can be configured to return the tractor to home position in a case where breakaway occurs.

The apparatus can further include a first arm, and a second arm, and a driving unit, wherein the first arm is connected to the driving unit that drives the first arm to the longitudinal direction, wherein the second arm is connected to the wire, and wherein the breakaway mechanism can include a breakaway connector configured to connect and disconnect the first arm and the second arm, wherein the second arm is moved to the longitudinal direction while the first arm and the second arm is connected by the breakaway connector and the first arm is driven by the driving unit.

According to some embodiments, a method can include moving a wire by an actuator along a longitudinal direction, connecting a tractor to the wire to move the wire along the longitudinal direction, providing a board that can include at least a first channel and a second channel, providing a plurality of sensors that can include at least a first sensor and a second sensor, arranging the first sensor and the second sensor at a different position from each other along a direction perpendicular to the longitudinal direction, causing the first sensor to determine a home position based on emitted light, and causing the second sensor to determine a limit position of travel based on emitted light.

According to some embodiments, a non-transitory storage medium storing a program can cause a computer to execute a method including moving a wire by an actuator along a longitudinal direction, connecting a tractor to the wire to move the wire along the longitudinal direction, providing a board that can include a first channel and a second channel, providing a plurality of sensors that can include at least a first sensor and a second sensor, arranging the first sensor and the second sensor at a different position from each other along a direction perpendicular to the longitudinal direction, causing the first sensor to determine a home position, and causing the second sensor to determine a limit position of travel based on emitted light.

Additional features or aspects of present disclosure can also advantageously implement one or more AI (artificial intelligence) or machine learning algorithms, processes, techniques, or the like, to re-engage breakaway and to integrate homing control and travel limiting control together to prevent the chance of a tractor experience of a crash situation where the tractor gets jammed. Such AI techniques use a neural network, a random forest algorithm, a cognitive computing system, a rules-based engine, or the like, and are trained based on a set of data to assess types of data and generate output. For example, a training algorithm can be configured to re-engage breakaway and to integrate homing control and travel limiting control together to prevent the chance of a tractor experience of a crash situation where the tractor gets jammed. The model(s) can be configured as software that takes images as input and returns predictions for the given images as output. The model(s) can be an instance of a model architecture (set of parameter values) that has been obtained by model training and selection using a machine learning and/or optimization algorithm/process. A model can generally include, for example, an architecture defined by a source code (e.g., a convolutional neural network including layers of parameterized convolutional kernels and activation functions, or the like) and configuration values (parameters, weights, features, or the like) that are initially set to random values and are then over the course of the training iteratively optimized given data example, an objective function (loss function), an optimization algorithm (optimizer), or the like.

At least some of the positional movement or orientation of actuator and other components to re-engage breakaway and to integrate homing control and travel limiting control together to prevent the chance of a tractor experience of a crash situation where the tractor gets jammed can be used as input data and provided to the training algorithm. Initial positional movement or orientation of the medical device can be stored in a database to facilitate precision centering of the fiber core relative to the ferrule outside diameter that are generated using input mapping to the model(s) or through expert research, and machine learning can find parameters for AI processes. Initial positional movement or orientation of the medical device are used or placed into an AI process or algorithm to facilitate precision modeling to accommodate various types of medical procedures, treatment, diagnostics, or another use. The training algorithm is configured to learn physical relationships in the input data to best describe these relationships or correlations. The data sets include information based on a number of factors including, for example, the positional movement or orientation of actuator and other components to re-engage breakaway and to integrate homing control and travel limiting control together to prevent the chance of a tractor experience of a crash situation where the tractor gets jammed, or the like. The data is evaluated using a weighted evaluation where the weights are learned through a training process, through subject matter specifications, or the like. Deep learning mechanisms can augment an AI process to accommodate various types of positional sensing and breakaway configurations, or another use.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

Other Embodiments

Embodiment(s) of the present disclosure can also be realized by a computerized configuration(s) of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computerized configuration(s) of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computerized configuration(s) may comprise one or more processors, one or more memories, circuitry, or a combination thereof (e.g., central processing unit (CPU), micro processing unit (MPU), or the like), and may include a network of separate computers or separate processors to read out and execute the computer executable instructions. The computer executable instructions may be provided to the computerized configuration(s), for example, from a network or the storage medium. The storage medium may include, for example, one or more of a hard-disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

What is claimed is:

1. An apparatus comprising:
   an actuator configured to move a wire along a longitudinal direction;
   a tractor that is connected to the wire and is configured to move the wire along the longitudinal direction;

a driving unit;

a first arm connected to the driving unit that drives the first arm along the longitudinal direction;

a board connected to the first arm;

a second arm connected to the wire;

a plurality of sensors comprising at least a first sensor and a second sensor arranged at a different position from each other along a direction perpendicular to the longitudinal direction, at least one positional sensor configured to determine position based on emitted light;

a support member configured to support at least one positional sensor; and a breakaway mechanism comprising a breakaway connector configured to connect and disconnect the first arm and the second arm.

2. The apparatus according to claim 1, wherein the breakaway mechanism is configured to disconnect the actuator and the tractor in a case where an applied force is greater than a predetermined value.

3. The apparatus according to claim 1, wherein the breakaway mechanism comprises a breakaway sensor configured to detect when breakaway occurs, wherein, in a case where breakaway detected by the breakaway sensor, a recovery and homing routine is initiated, and/or an error state can be initiated that can prompt a service technician or other to diagnose the apparatus.

4. The apparatus according to claim 1, wherein the breakaway mechanism is configured to return the tractor to home position in a case where breakaway occurs.

5. The apparatus according to claim 1, wherein the second arm is configured to move along the longitudinal direction while the first arm and the second arm is connected by the breakaway connector and the first arm is driven by the driving unit.

6. The apparatus according to claim 1, wherein the board comprises a first channel and a second channel.

7. The apparatus according to claim 6, wherein the first channel and the second channel of the board each have a length, wherein the length of the first channel is shorter than the length of the second channel.

8. The apparatus according to claim 6, wherein the first channel and the second channel of the board are configured to move along with movement of the tractor.

9. The apparatus according to claim 1, wherein the at least one positioning sensor comprises at least a first sensor and a second sensor that are arranged at a different position from each other along a direction perpendicular to the longitudinal direction.

10. The apparatus according to claim 1, wherein the wire comprises a plurality of wires.

11. The apparatus according to claim 1, further comprising one or more force sensors configured to measure push and pull forces on the wire.

12. The apparatus according to claim 1, further comprising one or more wire clamping mechanisms.

13. The apparatus according to claim 1, further comprising one or more linear sliding mechanisms.

14. The apparatus according to claim 1, further comprising a driving unit, wherein the first arm is connected to the driving unit that drives the first arm along the longitudinal direction, wherein the breakaway mechanism comprises a breakaway connector configured to connect and disconnect the first arm and the second arm, and wherein the second arm is moved along the longitudinal direction while the first arm and the second arm is connected by the breakaway connector and the first arm is driven by the driving unit.

15. The apparatus according to claim 1, wherein the board comprises a blocking board.

16. The apparatus according to claim 15, wherein the at least one positioning sensor comprises one or more sensors configured to detect light that is blocked by the blocking board and determine a home position.

17. The apparatus according to claim 15, wherein the at least one positioning sensor comprises one or more sensors configured to detect light that is blocked by the blocking board and determine a limit position of travel.

18. The apparatus according to claim 15, wherein the blocking board is configured to provide a negative limit transition and a positive limit and home transition.

19. The apparatus according to claim 15, further comprising a controller, wherein the blocking board comprises a first blocking board and a second blocking board, wherein in a case where a detection state of the at least one positioning sensor changes from a first state where a blocking of light by the first blocking board is detected to a second state where the blocking of the light by the first blocking board is not detected, the controller determines the tractor is at a home position, and wherein in a case where a detection state of the at least one positioning sensor changes from a third state where a blocking of light by the second blocking board is detected to a fourth state where the blocking of light by the second blocking board is not detected, the controller determines the tractor is at a limit position.

20. The apparatus according to claim 1, further comprising a first arm, and a second arm, and a driving unit, wherein the first arm is connected to the driving unit that drives the first arm to the longitudinal direction, wherein the second arm is connected to the wire, wherein the breakaway mechanism comprises a breakaway connector configured to connect and disconnect the first arm and the second arm, and wherein the second arm is moved to the longitudinal direction while the first arm and the second arm is connected by the breakaway connector and the first arm is driven by the driving unit.

21. A method comprising:

moving a wire by an actuator along a longitudinal direction;

connecting a tractor to the wire to move the wire along the longitudinal direction;

connecting a first arm to a driving unit that drives the first arm to the longitudinal direction;

connecting the first arm to a board;

connecting a second arm to the wire;

providing at least one positional sensor configured to determine position based on emitted light;

supporting the at least one positional sensor on a support member; and providing a breakaway mechanism comprising a breakaway connector configured to connect and disconnect the first arm and the second arm.

22. A non-transitory storage medium storing a program for causing a computer to execute a method comprising:

moving a wire by an actuator along a longitudinal direction;

connecting a tractor to the wire to move the wire along the longitudinal direction;

connecting a first arm to a driving unit that drives the first arm to the longitudinal direction;

connecting the first arm to a board;

connecting a second arm to the wire;

providing at least one positional sensor configured to determine position based on emitted light;

supporting the at least one positional sensor on a support member; and providing a breakaway mechanism comprising a breakaway connector configured to connect and disconnect the first arm and the second arm.

23. An apparatus comprising:

an actuator configured to move a wire along a longitudinal direction;

a tractor that is connected to the wire and is configured to move the wire along the longitudinal direction;

a board comprising at least a first channel and a second channel; and a plurality of sensors comprising at least a first sensor and a second sensor arranged at a different position from each other along a direction perpendicular to the longitudinal direction, wherein the first sensor is configured to determine a home position based on emitted light, and wherein the second sensor is configured to determine a limit position of travel based on emitted light.

24. The apparatus according to claim 23, wherein the board comprises a blocking board.

25. The apparatus according to claim 23, further comprising a controller, wherein the blocking board comprises a first blocking board and a second blocking board, wherein in a case where a detection state of the first sensor changes from a first state where a blocking of light by the first blocking board is detected to a second state where the blocking of the light by the first blocking board is not detected, the controller determines the tractor is at a home position, and wherein in a case where a detection state of the second sensor changes from a third state where a blocking of light by the second blocking board is detected to a fourth state where the blocking of light by the second blocking board is not detected, the controller determines the tractor is at a limit position.

26. The apparatus according to claim 23, wherein the board comprises a reflective board.

27. The apparatus according to claim 26, further comprising a controller, wherein the reflective board comprises a first reflective board and a second reflective board;

wherein in a case where a detection state of the first sensor changes from a first state where a reflection from the first reflective board is detected to a second state where the reflection from the first reflective board is not detected, the controller determines the tractor is at a home position, and wherein in a case where a detection state of the second sensor changes from a third state where a reflection from the second reflective board is detected to a fourth state where the reflection from the second reflective board is not detected, the controller determines the tractor is at a limit position.

* * * * *